(12) United States Patent
Hongo

(10) Patent No.: US 11,230,018 B2
(45) Date of Patent: Jan. 25, 2022

(54) PARALLEL LINK DEVICE, INDUSTRIAL ROBOT, AND HAPTIC PRESENTATION DEVICE

(71) Applicant: SONY CORPORATION, Tokyo (JP)

(72) Inventor: Kazuo Hongo, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 484 days.

(21) Appl. No.: 16/307,079

(22) PCT Filed: Jun. 28, 2017

(86) PCT No.: PCT/JP2017/023766
§ 371 (c)(1),
(2) Date: Dec. 4, 2018

(87) PCT Pub. No.: WO2018/008491
PCT Pub. Date: Jan. 11, 2018

(65) Prior Publication Data
US 2019/0329422 A1    Oct. 31, 2019

(30) Foreign Application Priority Data

Jul. 8, 2016    (JP) .............................. JP2016-135809

(51) Int. Cl.
*B25J 13/02*    (2006.01)
*B25J 9/00*    (2006.01)
(Continued)

(52) U.S. Cl.
CPC ............ *B25J 13/025* (2013.01); *B25J 9/0045* (2013.01); *B25J 9/06* (2013.01); *B25J 9/1065* (2013.01);
(Continued)

(58) Field of Classification Search
CPC ...... B25J 9/0045; B25J 9/0048; B25J 9/0051; B25J 9/06; B25J 9/1065; B25J 9/1623;
(Continued)

(56) References Cited

U.S. PATENT DOCUMENTS 5,587,937 A * 12/1996 Massie ................... B25J 9/1689
700/264
6,088,020 A *  7/2000 Mor ........................ G06F 3/016
318/628
(Continued)

FOREIGN PATENT DOCUMENTS

CN       1857875 A    11/2006
CN     101249654 A     8/2008
(Continued)

OTHER PUBLICATIONS

EPO Translation of the Description of JP 2001121460 A, Nagai, May 8, 2001. (Year: 2021).*

(Continued)

*Primary Examiner* — Daniel D Yabut
(74) *Attorney, Agent, or Firm* — Xsensus, LLP

(57) ABSTRACT

There is provided a parallel link device including a base, a plurality of arms each having at least four degrees of freedom and each including a first arm link, a second arm link, and a rotating joint, and a support which is coupled to an end of the second arm link of each of the plurality of the arms, and a position and a posture of which changes along with changes of posture of the plurality of the arms, where an axis of rotation (O7) of the rotating joint, which is coupled to the support and the second arm link, intersects or is adjacent to a rotational central point (Q) of the support.

17 Claims, 16 Drawing Sheets

(51) Int. Cl.
*B25J 9/06* (2006.01)
*B25J 9/16* (2006.01)
*B25J 9/10* (2006.01)
*G05G 1/01* (2008.04)
*G05G 1/015* (2008.04)
*A61B 34/00* (2016.01)

(52) U.S. Cl.
CPC ............. *B25J 9/1623* (2013.01); *B25J 13/02* (2013.01); *G05G 1/01* (2013.01); *G05G 1/015* (2013.01); *A61B 2034/742* (2016.02)

(58) Field of Classification Search
CPC ............ B25J 9/0042; B25J 9/003–0039; B25J 13/025; B25J 13/02; G05G 1/01; G05G 1/015; G05G 5/03
See application file for complete search history.

(56) References Cited

U.S. PATENT DOCUMENTS

| | | | | |
|---|---|---|---|---|
| 8,874,241 | B2* | 10/2014 | Yi | B25J 9/0048 700/3 |
| 8,950,286 | B2* | 2/2015 | Gosselin | B25J 3/04 74/490.06 |
| 2005/0252329 | A1* | 11/2005 | Demers | B25J 13/025 74/471 XY |
| 2007/0018958 | A1* | 1/2007 | Tavakoli | A61B 34/76 345/161 |
| 2009/0260473 | A1 | 10/2009 | Gosselin | |
| 2014/0144276 | A1* | 5/2014 | Yang | B25J 9/0009 74/490.03 |
| 2014/0150591 | A1* | 6/2014 | Yang | B25J 9/0048 74/490.03 |
| 2015/0151439 | A1 | 6/2015 | Gosselin | |
| 2017/0203433 | A1* | 7/2017 | Hongo | B25J 9/0045 |

FOREIGN PATENT DOCUMENTS

| | | |
|---|---|---|
| CN | 105269569 A | 1/2016 |
| JP | 11-254375 A | 9/1999 |
| JP | 2000-108061 A | 4/2000 |
| JP | 2000181618 A | 6/2000 |
| JP | 2001-121460 A | 5/2001 |
| JP | 2002178290 A | 6/2002 |
| JP | 2005052946 A | 3/2005 |
| JP | 2009-279659 A | 12/2009 |
| JP | 2009-545459 A | 12/2009 |
| JP | 4468056 B2 | 5/2010 |
| JP | 4659098 B2 | 3/2011 |
| JP | 2011-230241 A | 11/2011 |
| WO | 2012/103648 A1 | 8/2012 |
| WO | WO 2012/103648 A1 | 8/2012 |

OTHER PUBLICATIONS

EPO Translation of the Description of JP 2000181618 A, Okazaki et al., May 8, 2001. (Year: 2021).*
Office Action dated May 26, 2020, issued in Japanese Patent Application No. 2016-135809, 9 pages.
Decision of Rejection dated Aug. 4, 2020, issued in corresponding Japanese Patent Application No. 2016-135809, 4 pages.
International Search Report dated Dec. 12, 2017 in PCT/JP2017/023766, 3 pages.

* cited by examiner

[Fig. 1]
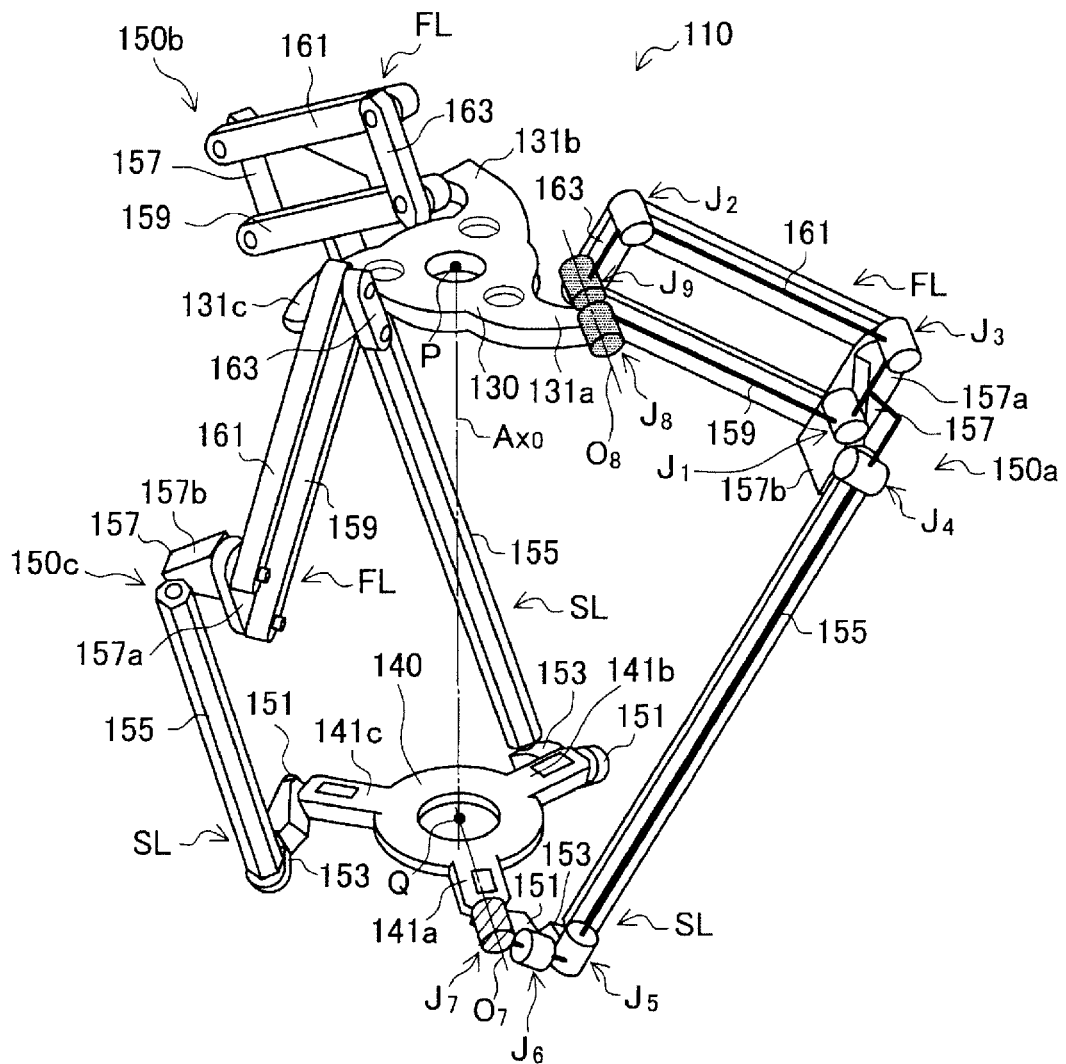

[Fig. 2]
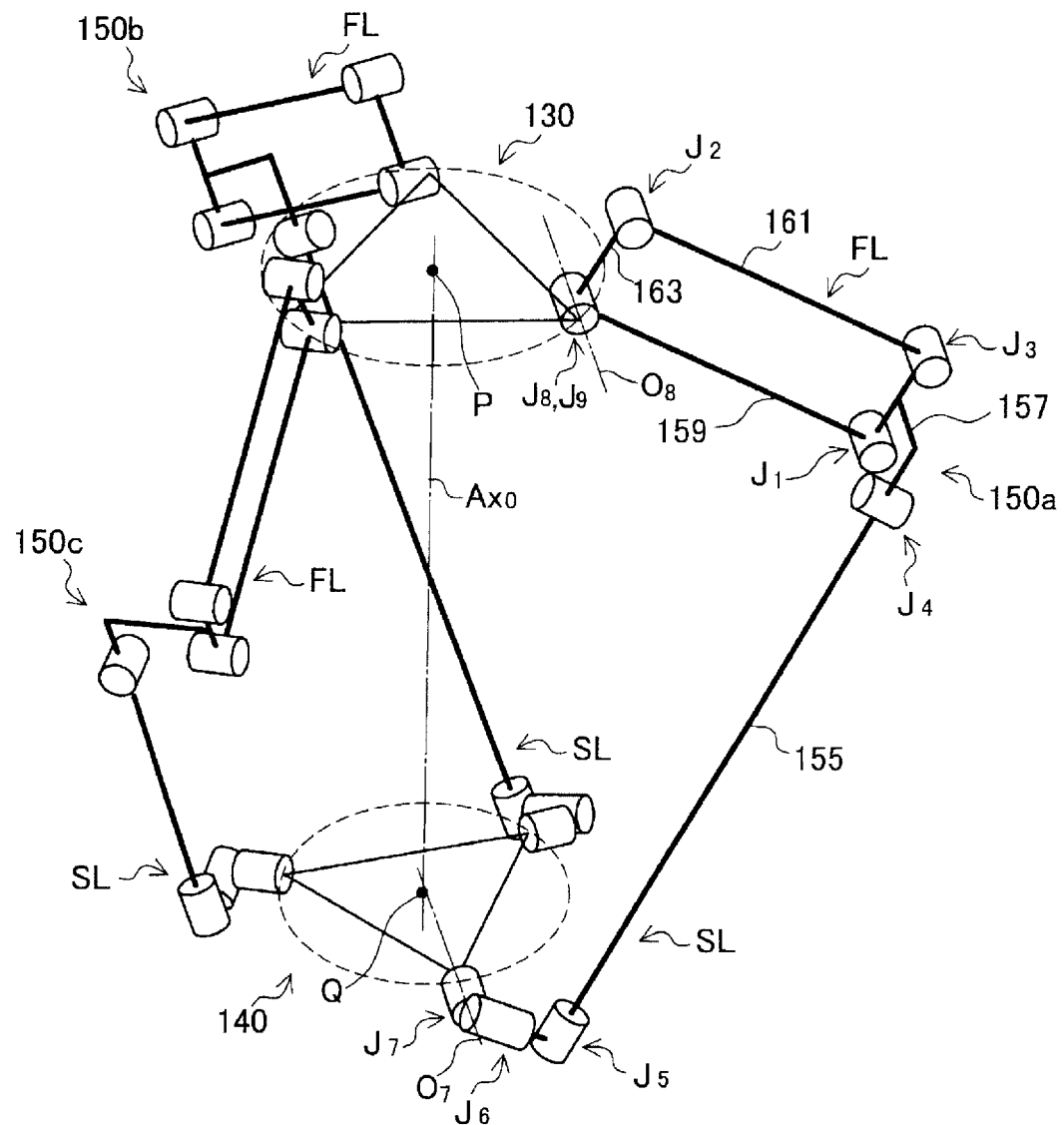

[Fig. 3]
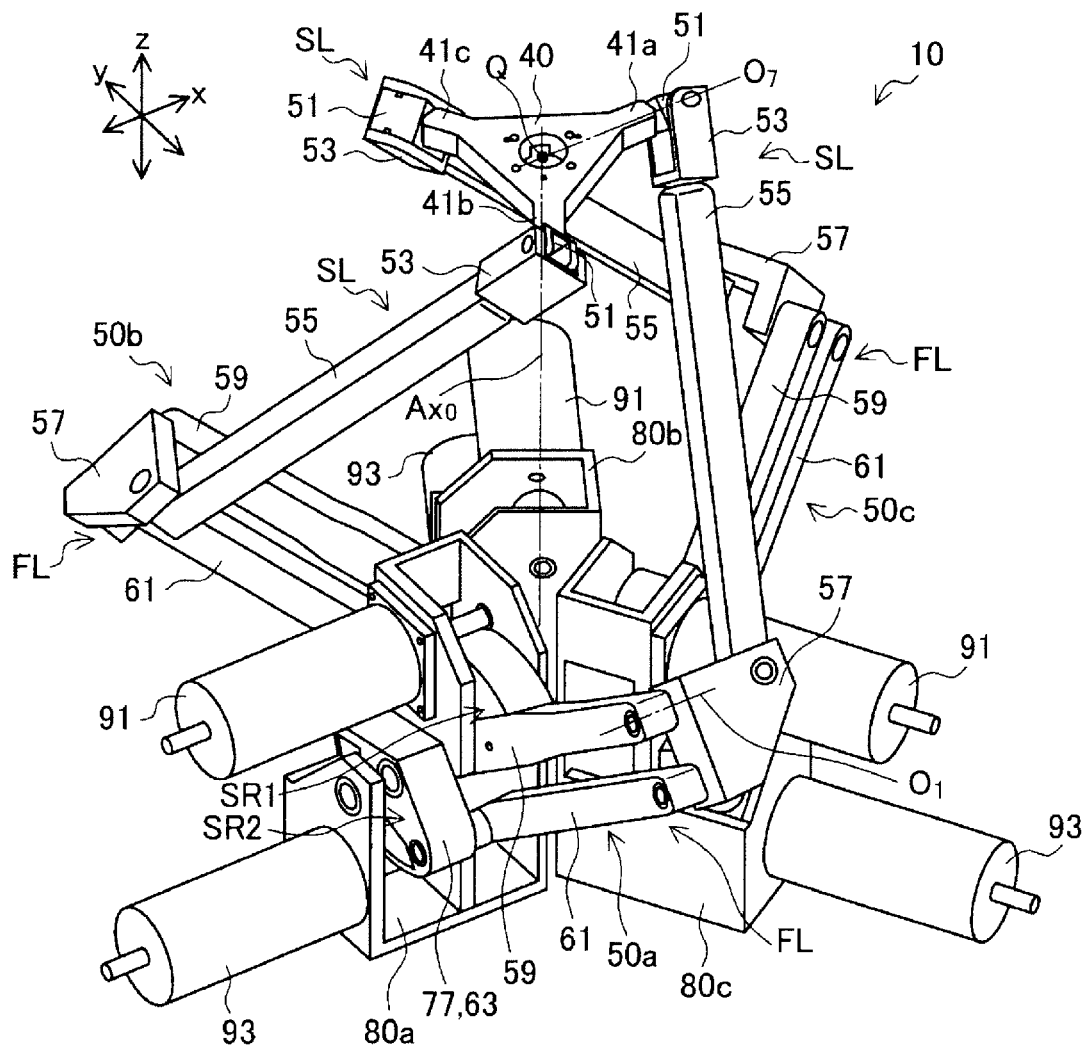

[Fig. 4]
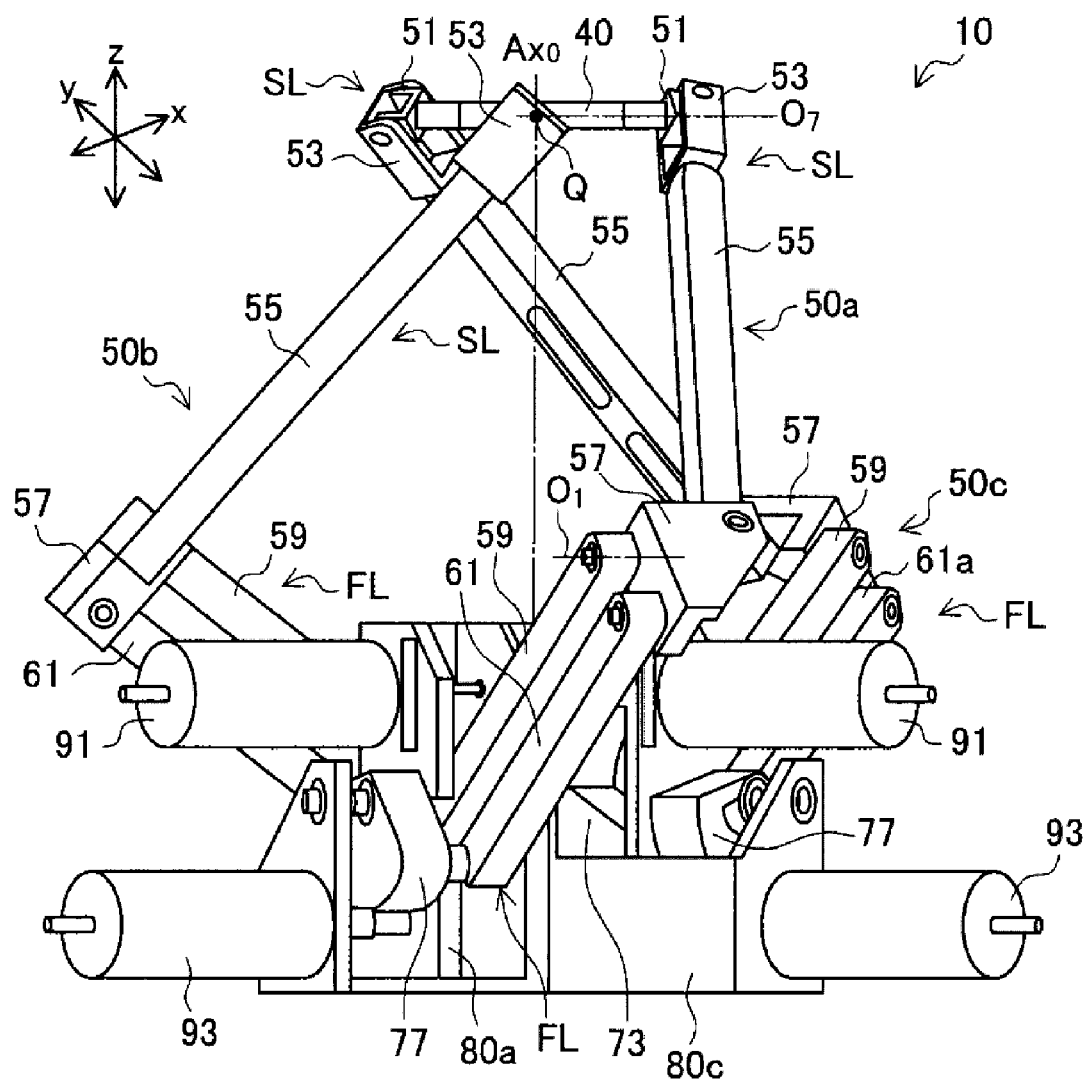

[Fig. 5]
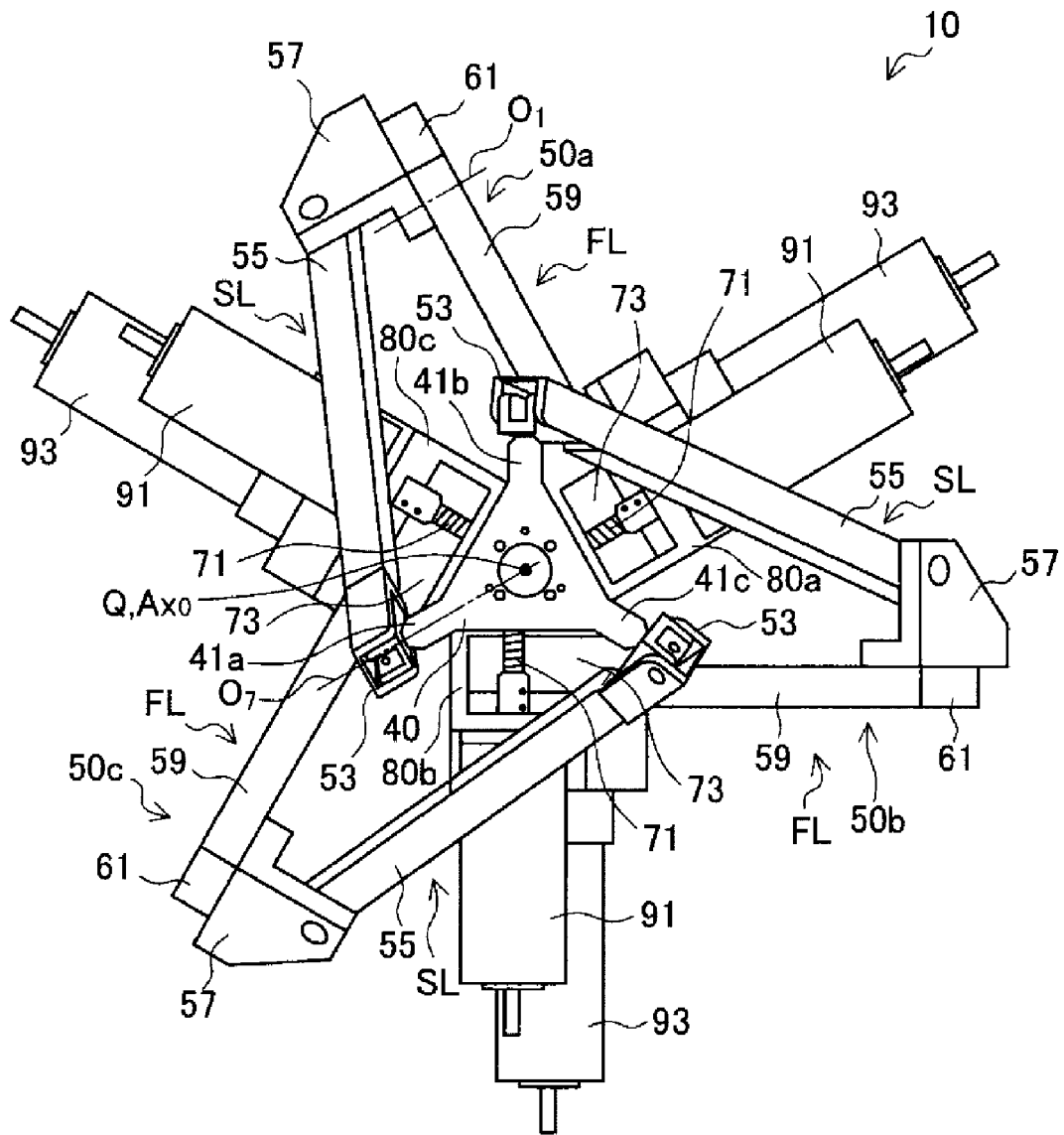

[Fig. 6]
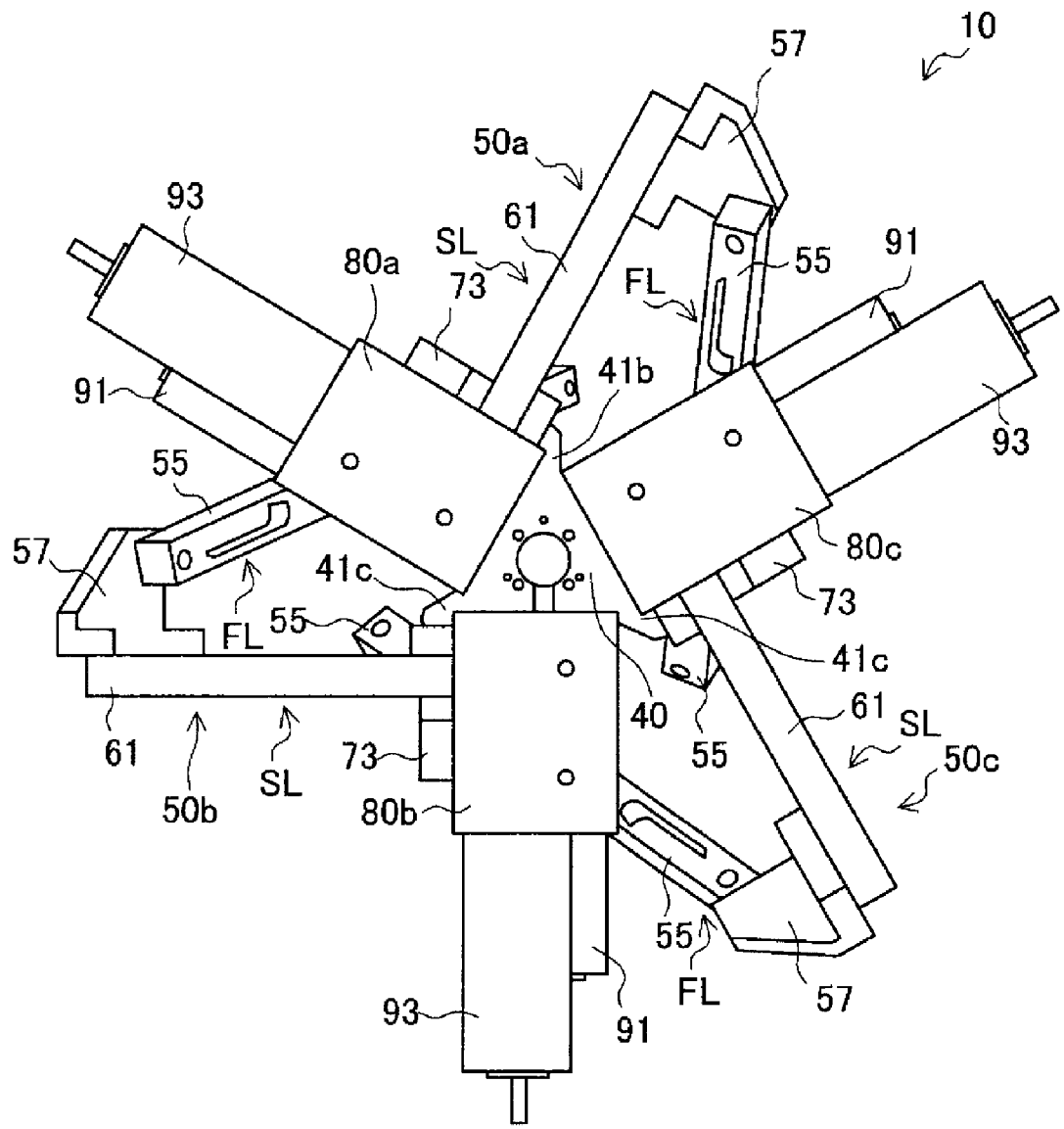

[Fig. 7]
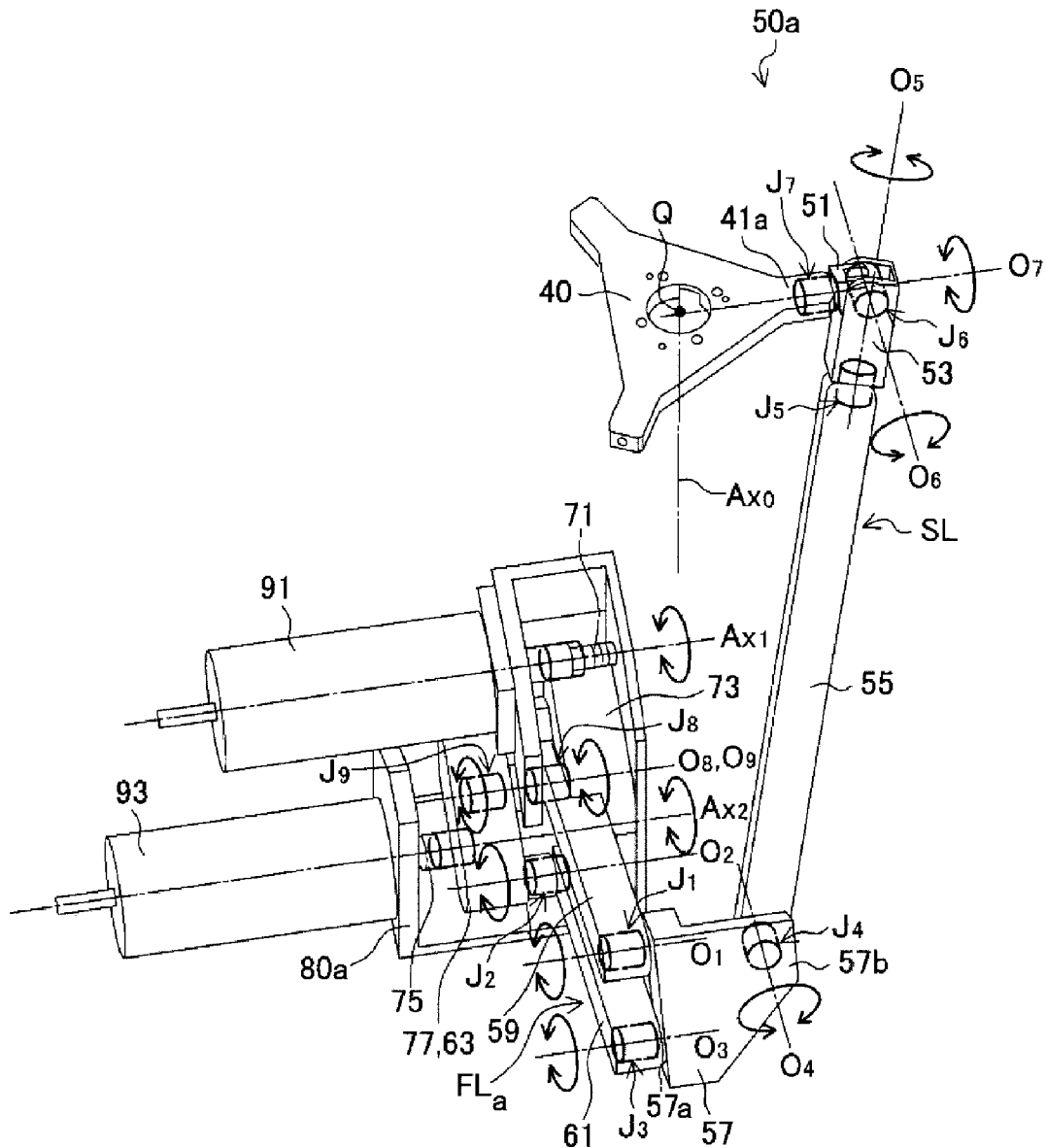

[Fig. 8]
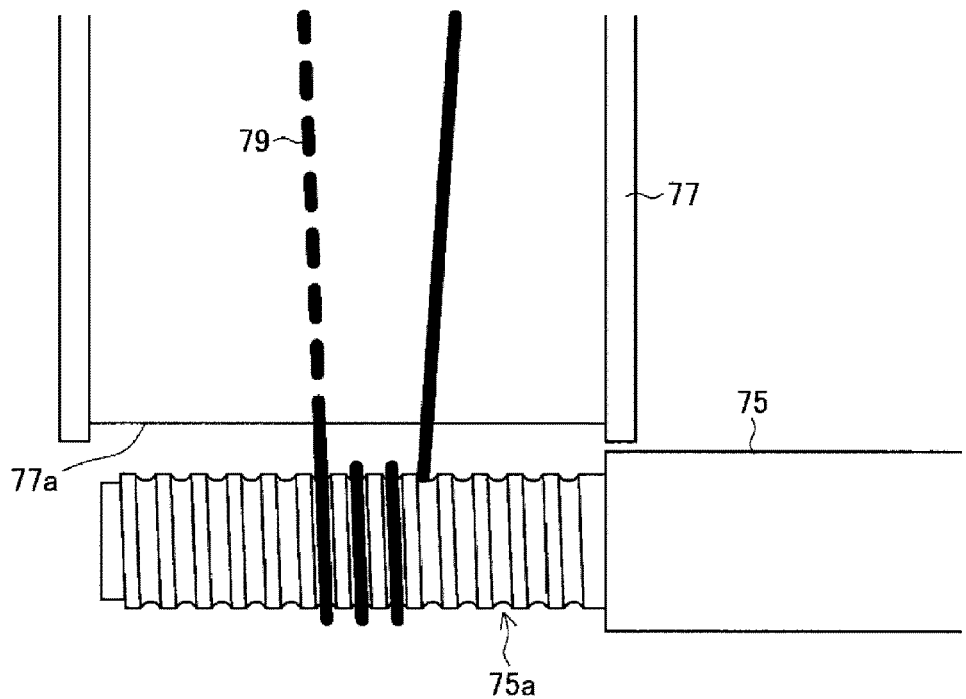
[Fig. 9]
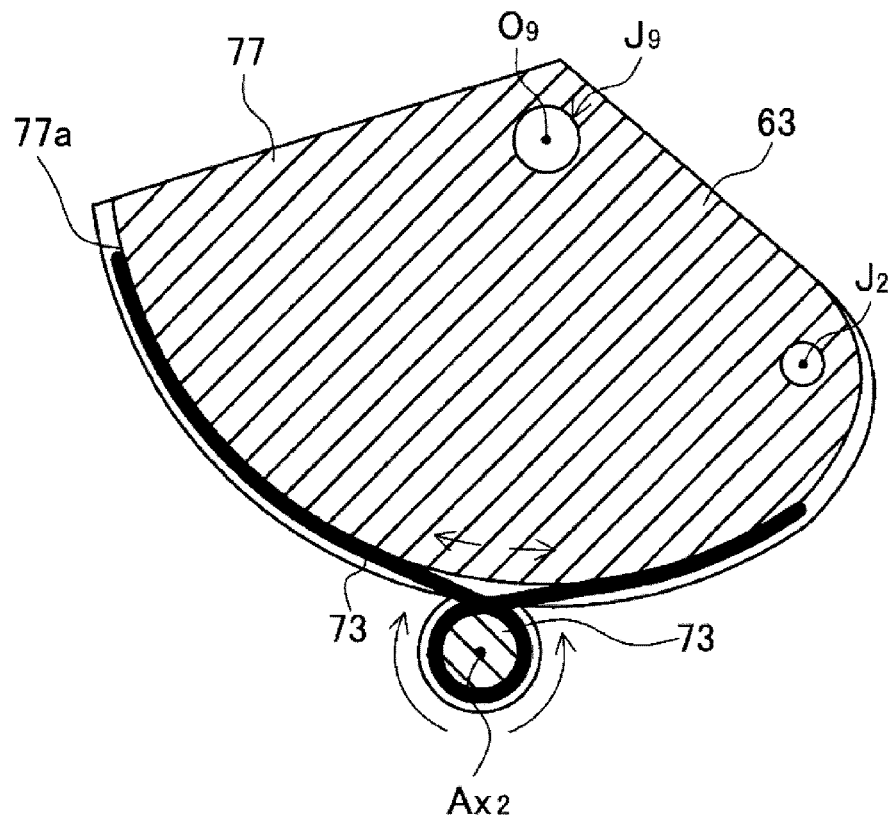

[Fig. 10]
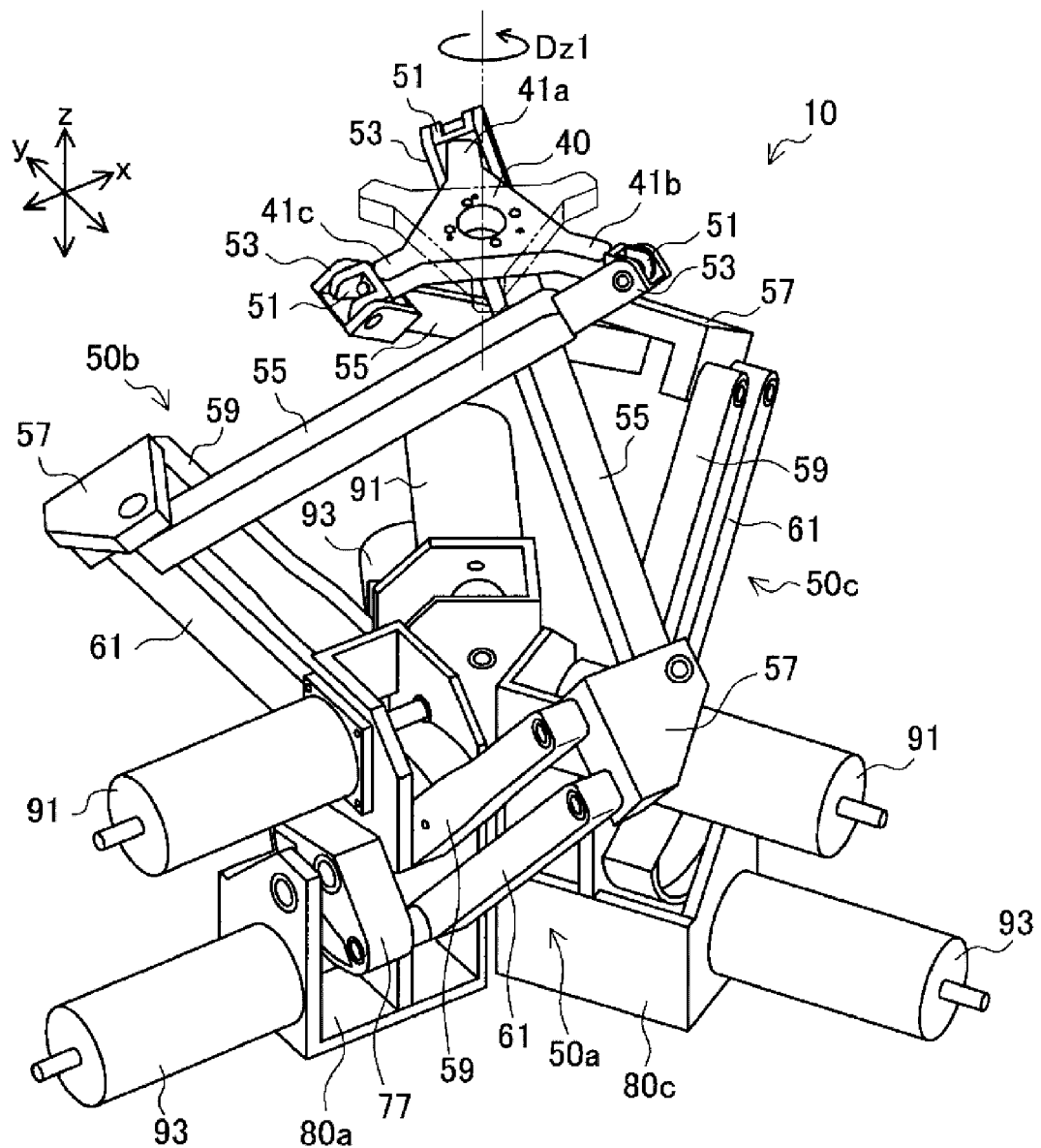

[Fig. 11]
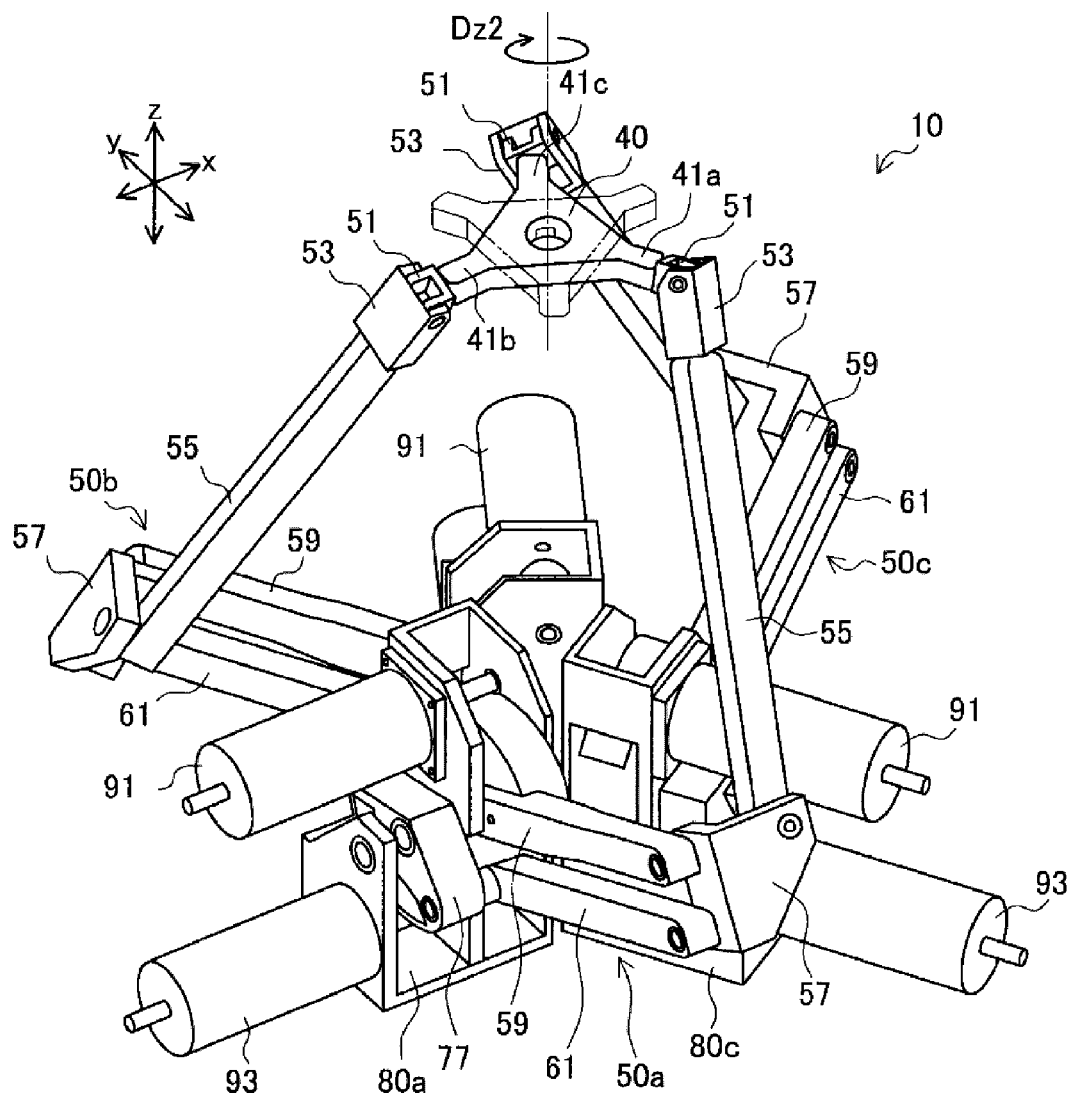

[Fig. 12]
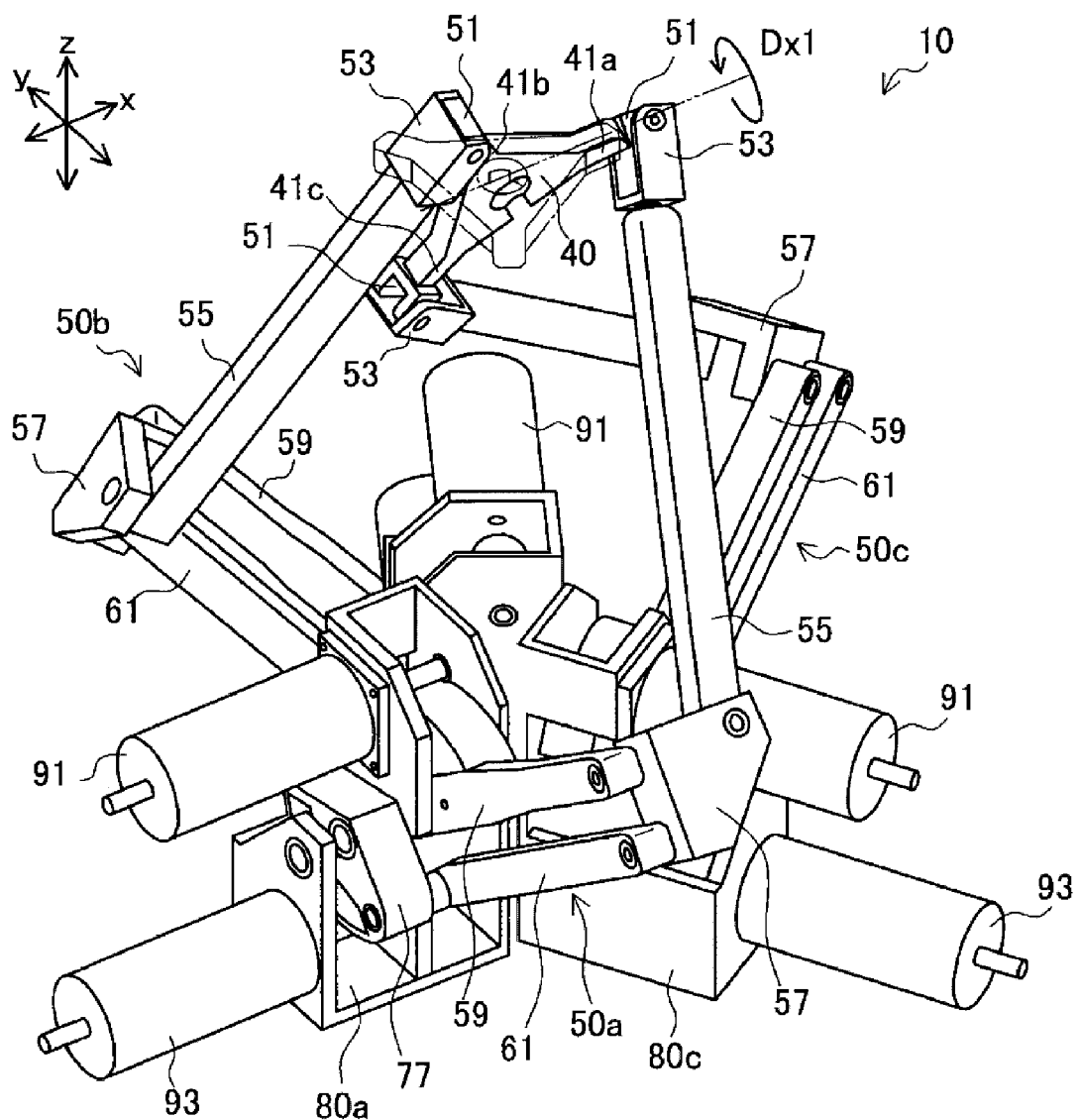

[Fig. 13]
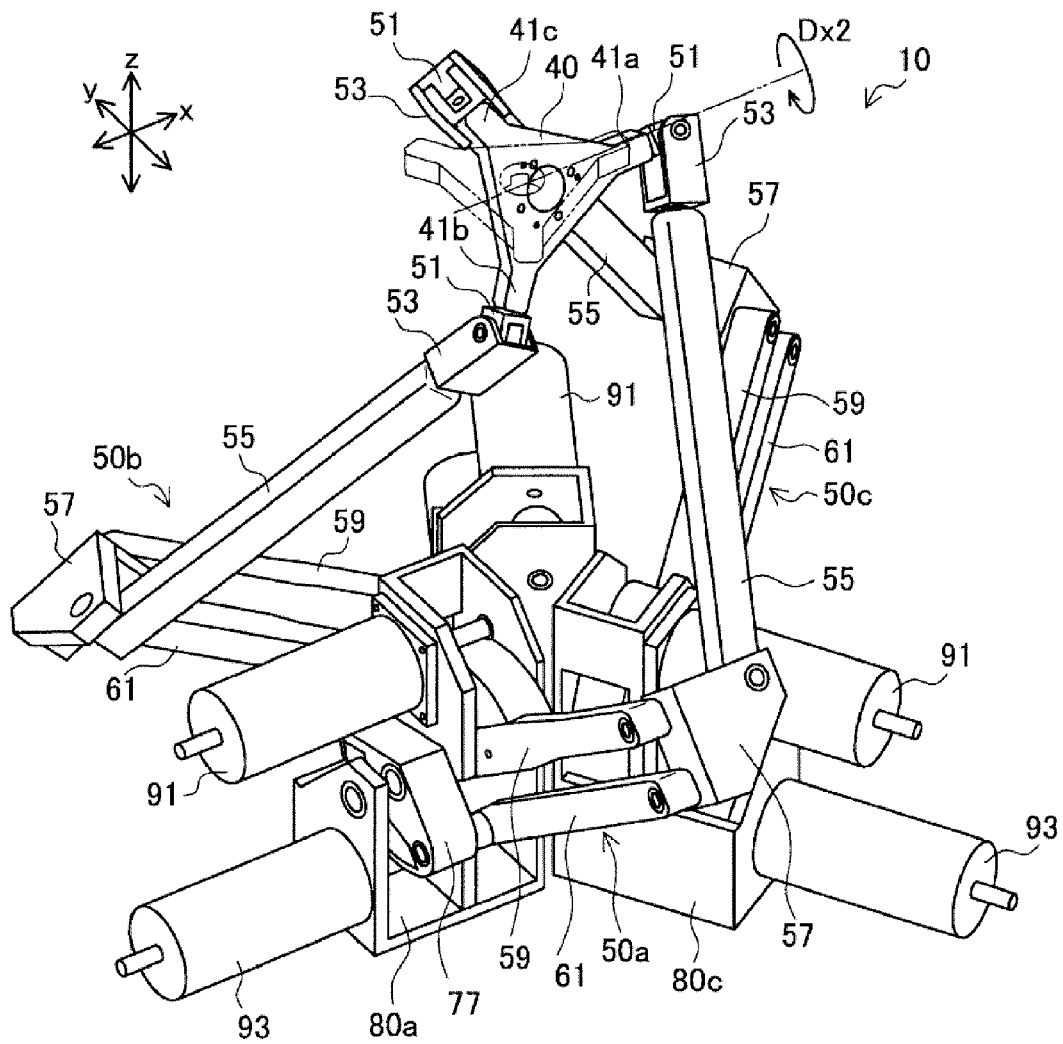

[Fig. 14]
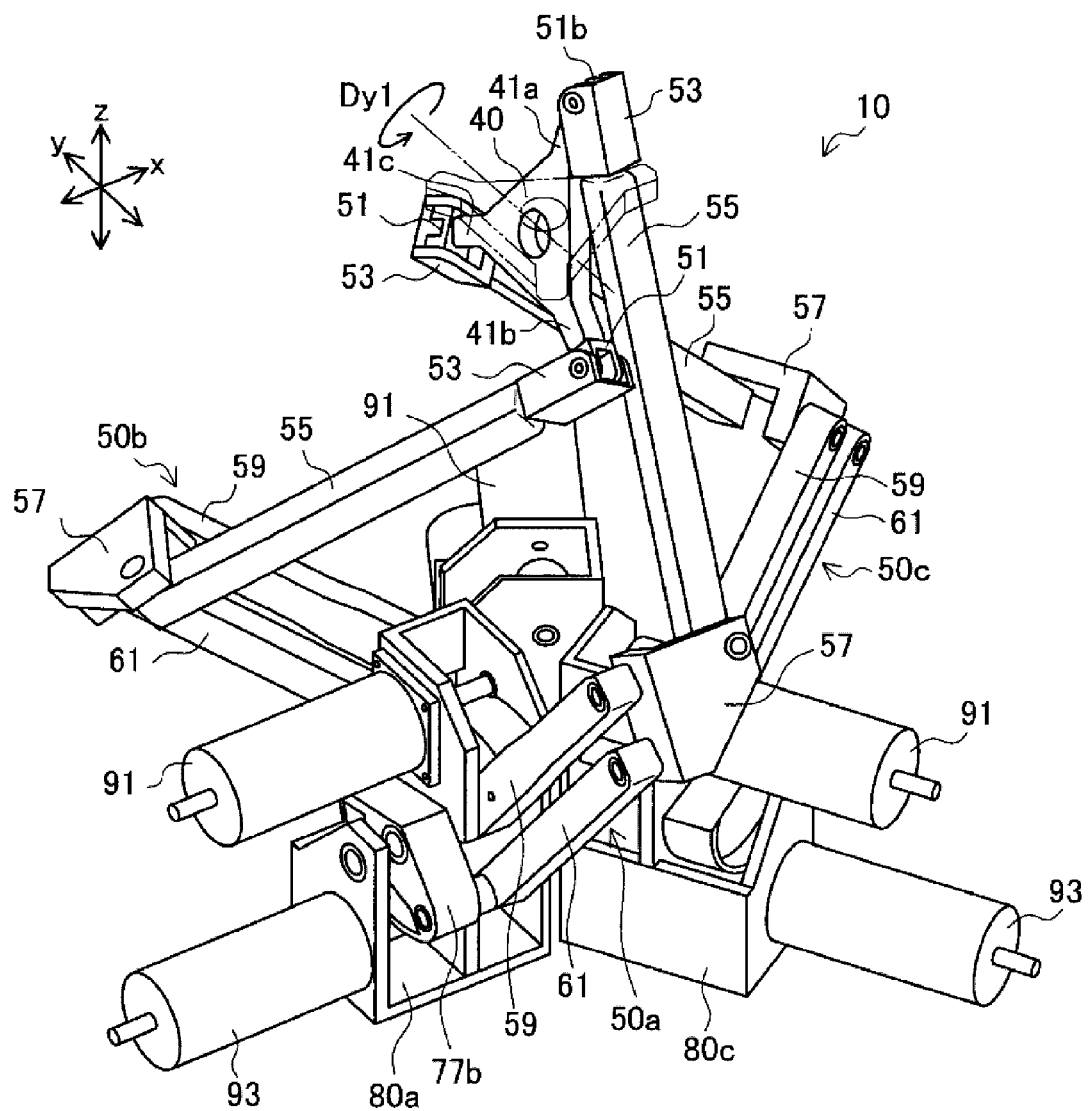

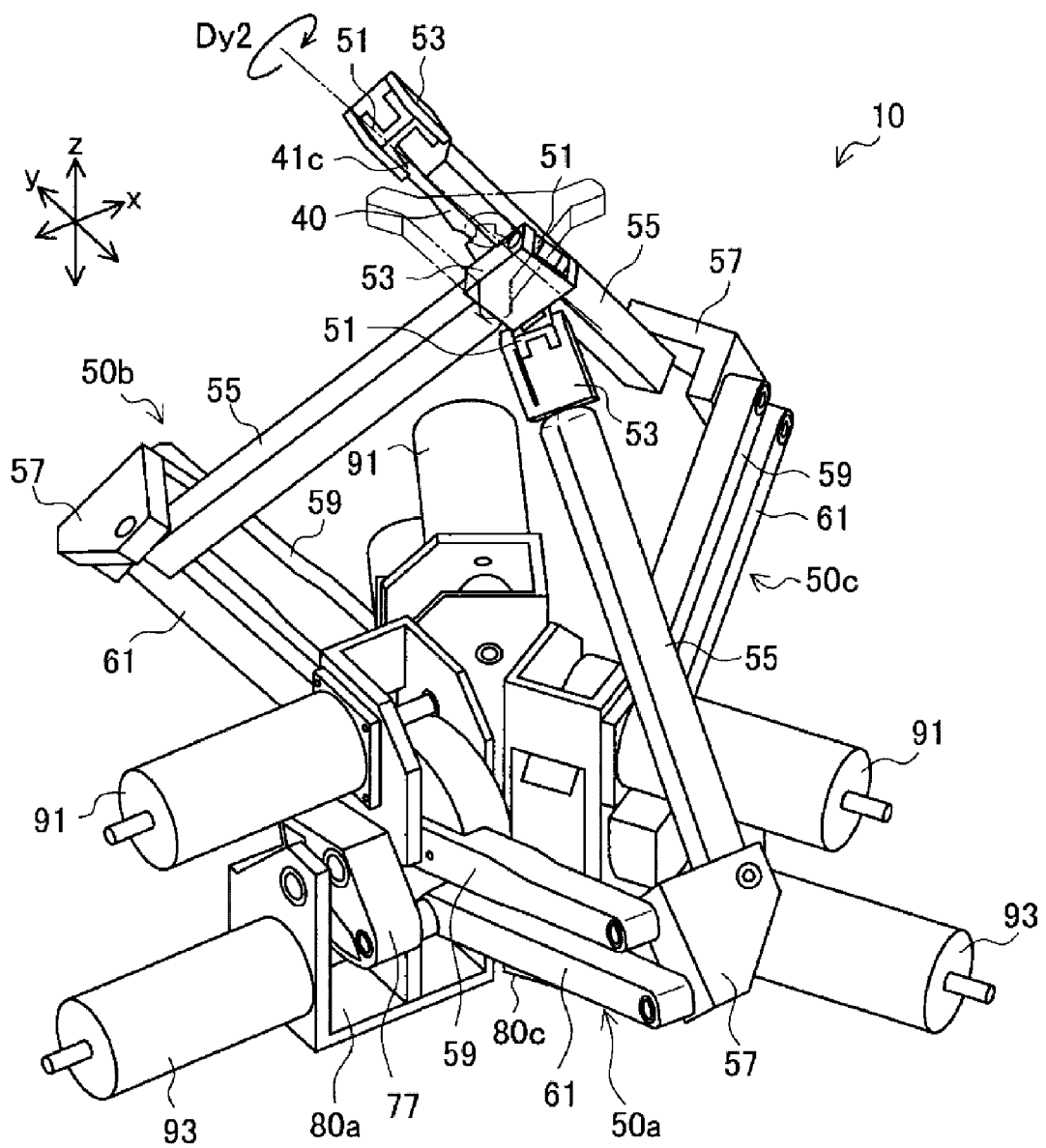
[Fig. 15]

[Fig. 16]
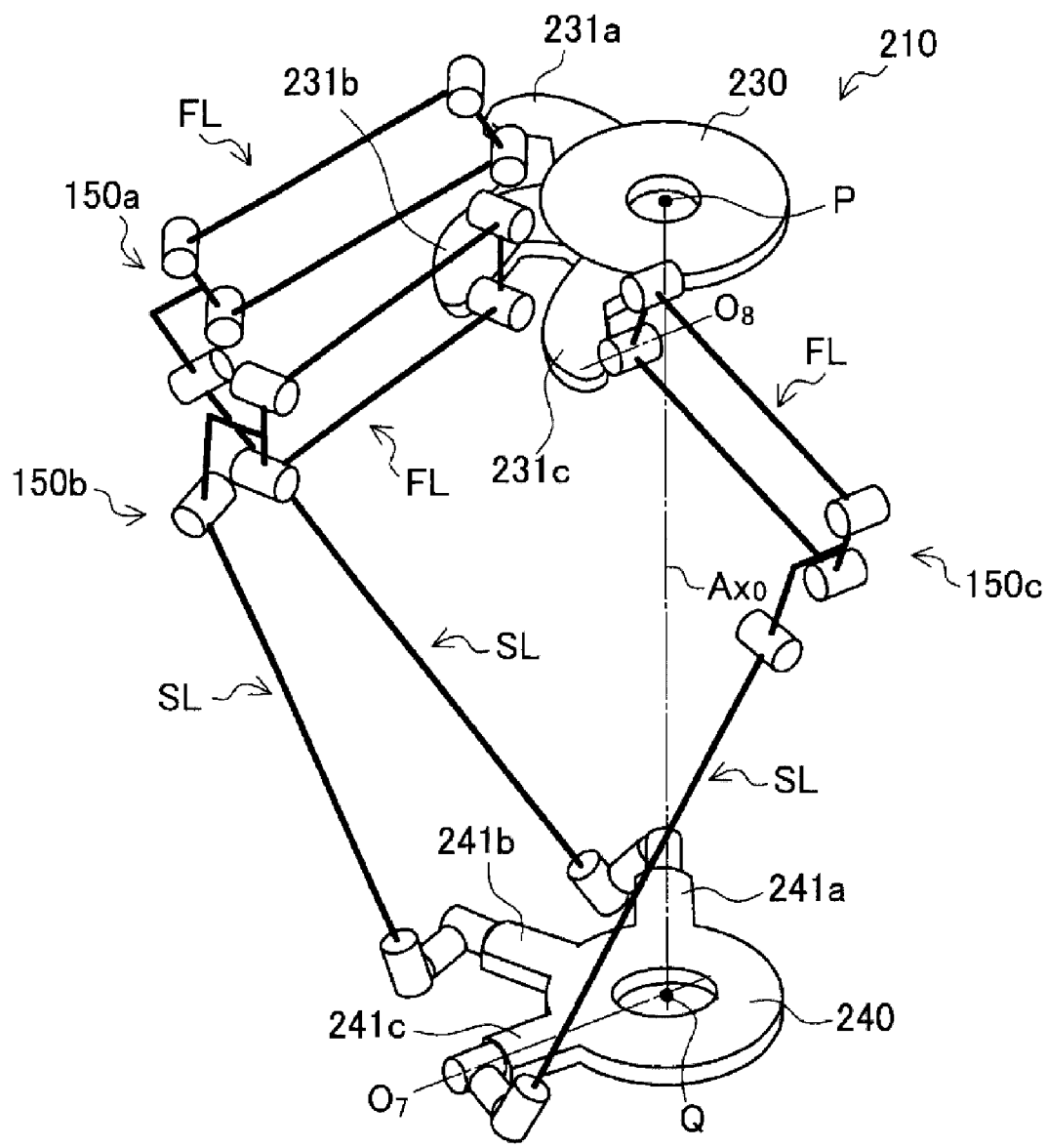

[Fig. 17]
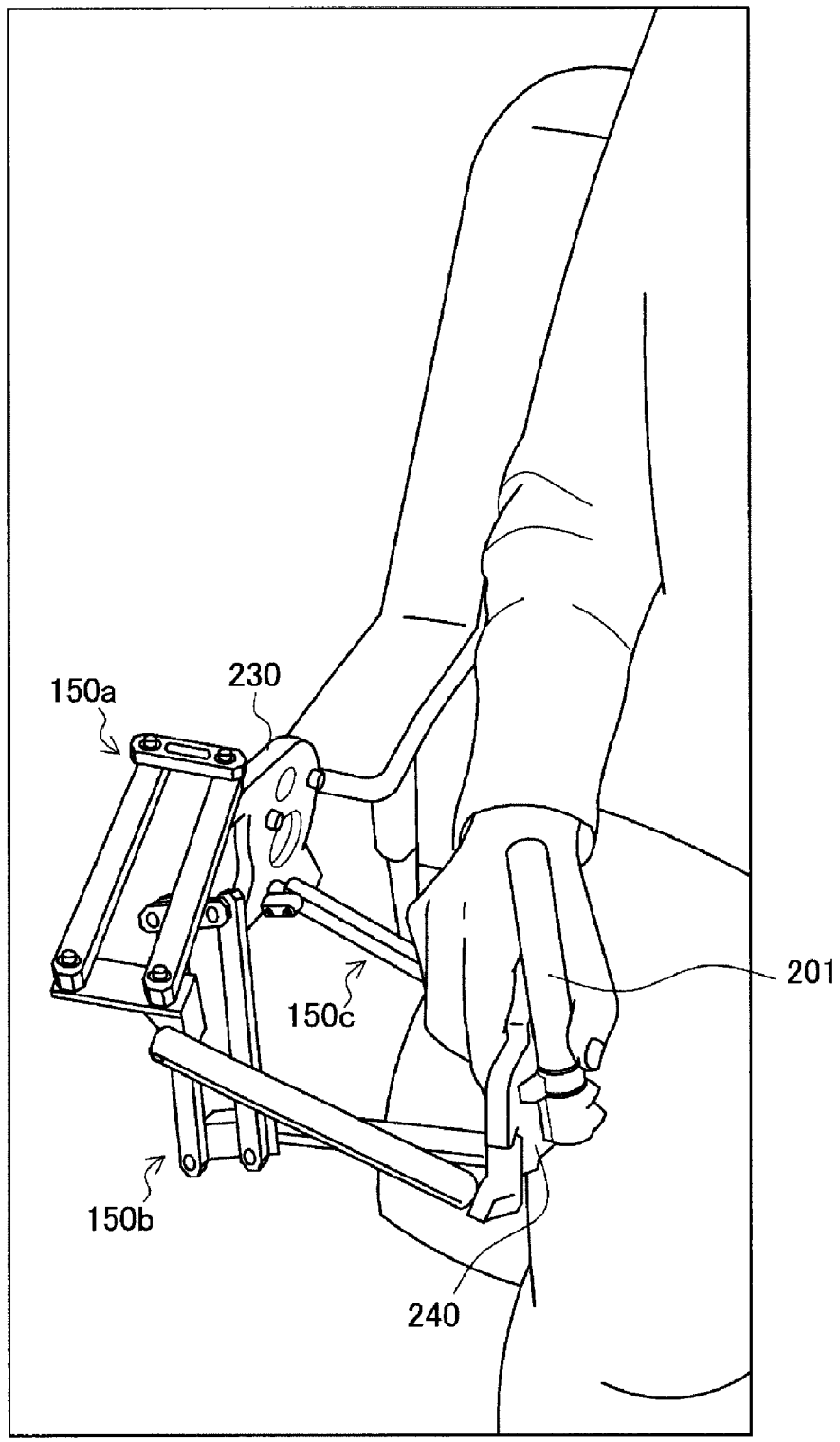

PARALLEL LINK DEVICE, INDUSTRIAL ROBOT, AND HAPTIC PRESENTATION DEVICE

CROSS REFERENCE TO RELATED APPLICATIONS

This application claims the benefit of Japanese Priority Patent Application JP 2016-135809 filed Jul. 8, 2016, the entire contents of which are incorporated herein by reference.

TECHNICAL FIELD

This disclosure relates to a parallel link device, an industrial robot, and a haptic presentation device.

BACKGROUND ART

In recent years, robots in which parallel links are adopted have received attention as industrial robots. Such parallel link robots have characteristics that distal end sides of a plurality of arm parts constituting parallel links can be constituted to be relatively light and can be produced at relatively low cost. Furthermore, parallel link robots also have characteristics that, since actuators such as motors can be disposed at a base side instead of distal end sides of arm parts; it is difficult for the weight of the actuators themselves to cause a large load on outputs of the actuators. In addition, since distal end sides of parallel link robots can be constituted to be relatively light and thus the inertia thereof can made smaller, parallel link robots are used as user interfaces also in medical applications.

As a parallel link structure in the related art, a delta type and a hexa type parallel link structure are known. For example, PTL 1 discloses a hexa type parallel link device including three arm parts, each of which is driven through two motors. In a parallel link device disclosed in PTL 1, motions with six degrees of freedom are possible in a relatively simple structure and thus a range of motion of a translational motion of a movable plate becomes relatively larger. However, in such a parallel link device, while a range of motion of a translational motion of a movable plate is large, a range of motion of a rotational motion is small, and a limit of a range of motion is about ±60 degrees with respect to a roll angle, a pitch angle, and a yaw angle at a central position serving as a reference for a range of motion of a movable plate.

Also, PTL 2 discloses a parallel link device with a three axis rotating structure. In the parallel link device disclosed in PTL 2, a range of motion of a rotational motion of an output member is relatively large and a structure in which only a rotational motion of the output member is possible and a translational motion is impossible is provided.

PTL 3 discloses a parallel link device with a six axis parallel link structure. In the parallel link device disclosed in PTL 3, a range of motion of a rotational motion of a movable member is relatively large and a translational motion is possible. However, in such a parallel link device, a translational motion of a movable member is produced through a parallel link structure, a rotational motion is realized in a serial structure, and thus all of the force of six motors cannot be used as a driving force at a distal end side. Furthermore, it can be said that the inertia at the distal end side of such a parallel-serial composite structure may easily become relatively large.

CITATION LIST

Patent Literature

PTL 1: JP 2011-230241A
PTL 2: JP 4468056
PTL 3: JP 4659098

SUMMARY

Technical Problem

In order to increase the usability of a parallel link device, it is preferable to increase all of ranges of motion of translational motions with three degrees of freedom and rotational motions with three degrees of freedom while utilizing characteristics of a parallel link structure such as the fact that a distal end side can be constituted to be lighter, the fact that inertia at the distal end side can be decreased, and the fact that a load of a motor can be decreased.

Thus, this disclosure proposes a novel and improved parallel link device, industrial robot, and haptic presentation device which can perform translational motions with three degrees of freedom and rotational motions with three degrees of freedom of a movable member in a wide range of motion.

Solution to Problem

According to an embodiment of the present disclosure, there is provided a parallel link device including: a base, a plurality of arms each having at least four degrees of freedom and each including a first arm link, a second arm link, and a rotating joint, and a support which is coupled to an end of the second arm link of each of the plurality of the arms, and a position and a posture of which changes along with changes of posture of the plurality of the arms, where an axis of rotation (O7) of the rotating joint, which is coupled to the support and the second arm link, intersects or is adjacent to a rotational central point (Q) of the support.

Further, according to an embodiment of the present disclosure, there is provided an industrial robot including: a parallel link device including a base, a plurality of arms each having at least four degrees of freedom and each including a first arm link, a second arm link, and a rotating joint, and a support which is coupled to an end of the second arm link of each of the plurality of the arms, and a position and a posture of which changes along with changes of posture of the plurality of the arms, where an axis of rotation (O7) of the rotating joint, which is coupled to the support and the second arm link, intersects or is adjacent to a rotational central point (Q) of the support.

Further, according to an embodiment of the present disclosure, there is provided a haptic presentation device including: a parallel link device including a base, a plurality of arms each having at least four degrees of freedom and each including a first arm link, a second arm link, and a rotating joint, and a support which is coupled to an end of the second arm link of each of the plurality of the arms, and a position and a posture of which changes along with changes of posture of the plurality of the arms, where an axis of rotation (O7) of the rotating joint that is coupled to the support and the second arm link, intersects or is adjacent to a rotational central point (Q) of the support.

Advantageous Effects of Invention

As described above, according to this disclosure, translational motions with three degrees of freedom and rotational motions with three degrees of freedom of a movable member of a parallel link device can be performed in a wide range of motion.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is a schematic diagram illustrating one configuration example of a parallel link device related to a first embodiment of this disclosure.

FIG. 2 is an explanatory diagram showing a structure of the parallel link device related to the embodiment.

FIG. 3 is a perspective view illustrating another configuration example of the parallel link device related to the embodiment.

FIG. 4 is a side view illustrating another configuration example of the parallel link device.

FIG. 5 is a plan view of the parallel link device of the other configuration example when viewed from a movable member side.

FIG. 6 is a plan view of the parallel link device of the other configuration example when viewed from a base part side.

FIG. 7 is an explanatory diagram showing an arm part.

FIG. 8 is an explanatory diagram illustrating a speed reduction mechanism of a motor.

FIG. 9 is an explanatory diagram illustrating a speed reduction mechanism of a motor.

FIG. 10 is an explanatory diagram illustrating a rotational motion of a movable member.

FIG. 11 is an explanatory diagram illustrating a rotational motion of a movable member.

FIG. 12 is an explanatory diagram illustrating a rotational motion of a movable member.

FIG. 13 is an explanatory diagram illustrating a rotational motion of a movable member.

FIG. 14 is an explanatory diagram illustrating a rotational motion of a movable member.

FIG. 15 is an explanatory diagram illustrating a rotational motion of a movable member.

FIG. 16 is an explanatory diagram illustrating a structure of a parallel link device related to a second embodiment of this disclosure.

FIG. 17 is an explanatory diagram illustrating a usage example of the parallel link device related to the embodiment.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.

1. First Embodiment
   1-1. Schematic configuration example of parallel link device
   1-2. Specific configuration example of parallel link device
   1-3. Motion of parallel link device
   1-4. Usage modes of parallel link device
   1-5. Application examples
   1-6. Conclusion
2. Second Embodiment

1. First Embodiment

<1-1. Schematic Configuration Example of Parallel Link Device>

Referring to FIGS. 1 and 2, an example of a schematic configuration of a parallel link device 110 related to a first embodiment of this disclosure will be described. FIG. 1 is a schematic configuration diagram illustrating one configuration example of the parallel link device 110 related to this embodiment. FIG. 2 is an explanatory diagram illustrating a structure of the parallel link device 110.

Note that, in a base part and a movable member of a parallel link device in this specification, the movable member side thereof is referred to as a front or distal side and the base part side thereof is referred to as a rear or proximal end side.

The parallel link device 110 related to this embodiment includes a base plate 130 serving as the base part (base), a movable plate 140 serving as the movable member (support), and a first arm part 150a (first arm), a second arm part 150b (second arm), and a third arm part 150c (third arm) serving as a plurality of arm parts. The first arm part 150a, the second arm part 150b, and the third arm part 150c are connected in parallel between the base plate 130 and the movable plate 140.

The base plate 130 can be fixed to a bogie, a supporting table, a supporting wall, a supporting column, a supporting beam, a ceiling, a floor surface, or the like (not shown) at the time of use. Proximal end sides of the first arm part 150a, the second arm part 150b, and the third arm part 150c are coupled to fixed parts 131a, 131b, and 131c of the base plate 130 provided around a rotational central point P thereof at equal intervals every 120 degrees. The rotational central point P is a rotational central point of coupling positions between the base plate 130 and the first arm part 150a, the second arm part 150b, and the third arm part 150c. A shape of the base plate 130 is not particularly limited.

Also, distal end sides of the first arm part 150a, the second arm part 150b, and the third arm part 150c are coupled to fixed parts 141a, 141b, and 141c of the movable plate 140 provided around a rotational central point Q thereof at equal intervals every 120 degrees. The rotational central point Q is a rotational central point of coupling positions between the movable plate 140 and the first arm part 150a, the second arm part 150b, and the third arm part 150c. A shape of the movable plate 140 is not particularly limited.

In the parallel link device 110 shown in FIG. 1, the first arm part 150a, the second arm part 150b, and the third arm part 150c have the same configuration. A configuration example of the arm parts will be described using the first arm part 150a among them as an example. The first arm part 150a includes a four-joint link mechanism FL (first arm link) coupled to the fixed part 131a of the base plate 130 and a serial link mechanism SL (second arm link), a proximal end side of which is coupled to the four-joint link mechanism FL and a distal end side of which is coupled to the movable plate 140.

The four-joint link mechanism FL includes a first link 159, a second link 163, a third link 161 and a fourth link 157. The first link 159 is coupled to the fixed part 131a of the base plate 130 via a first active joint $J_8$ serving as a uniaxially rotated joint. The first active joint $J_8$ may be an output shaft of a first motor (not shown) serving as an actuator and the first link 159 may be rotatably driven through the first motor. Furthermore, the second link 163 is coupled to the fixed part 131a of the base plate 130 via a second active joint $J_9$ serving as a uniaxial active joint. The second active joint $J_9$ may be an output shaft of a second motor (not shown) different from the first motor and the second link 163 may be rotatably driven through the second motor.

The first active joint $J_8$ and the second active joint $J_9$ may not be output shafts themselves of motors, may be coupled to output shafts of motors via gears or the like, and may be rotating shafts configured to rotate through rotational driving of the first motor and the second motor. Representative examples of an actuator include a rotating motor such as a stepping motor, a servo motor, and a direct current motor. Here, any linear motor which includes a mechanism configured to covert a linear motion into a rotational motion may be used.

The first link 159 is coupled to the fourth link 157 through a first rotating joint $J_1$ serving as a uniaxially rotated joint. Furthermore, the second link 163 is coupled to the third link 161 through a second rotating joint $J_2$ serving as a uniaxially rotated joint and the third link 161 is coupled to the fourth link 157 through a third rotating joint $J_3$ serving as a uniaxially rotated joint. The first rotating joint $J_1$, the second rotating joint $J_2$, the third rotating joint $J_3$, and the first active joint $J_8$ have axes of rotation parallel to each other. Thus, the first link 159, the second link 163, the third link 161, and the fourth link 157 can constitute the four-joint link mechanism FL. In the illustrated example of the parallel link device 110, the first active joint $J_8$ and the second active joint $J_9$ are disposed to be coaxial with each other. Here, the second active joint $J_9$ and the first active joint $J_8$ may not be coaxial with each other as long as the second active joint $J_9$ is disposed to be parallel to the first active joint $J_8$.

In the parallel link device 110 related to this embodiment, a distance L1 between the rotating shaft of the first active joint $J_8$ and the rotating shaft of the first rotating joint $J_1$ is the same as a distance L2 between the rotating shaft of the second rotating joint $J_2$ and the rotating shaft of the third rotating joint $J_3$ (refer to FIG. 2). Furthermore, a distance L3 between the rotating shaft of the second active joint $J_9$ and the rotating shaft of the second rotating joint $J_2$ is the same as a distance L4 between the rotating shaft of the first rotating joint $J_1$ and the rotating shaft of the third rotating joint $J_3$ (refer to FIG. 2). In other words, the four-joint link mechanism FL of the first arm part 150a is constituted as a parallel link mechanism. A parallel link mechanism is a link mechanism in which a parallelogram or a diamond is formed through a plurality of links. The fourth link 157 of the four-joint link mechanism FL is controlled with two degrees of freedom through driving control of the first motor and the second motor.

Note that, although the four-joint link mechanism FL may not be a parallel link mechanism, it is easy to control a structure design of the parallel link device 110 and a position and a posture of the movable plate 140 as long as the four-joint link mechanism FL is a parallel link mechanism.

The fourth link 157 of the four-joint link mechanism FL is an L-shaped right angle link A shape of the fourth link 157 is not limited to an L shape and may be, for example, a T shape. A fourth rotating joint $J_4$ serving as a uniaxially rotated joint is provided in the L-shaped fourth link 157 from a portion 157a located between the first rotating joint $J_1$ and the third rotating joint $J_3$ of the four-joint link mechanism FL to a portion 157b extending in a direction orthogonal to a plane formed by the four-joint link mechanism FL. The axis of rotation of the fourth rotating joint J4 is orthogonal to the axes of rotation of the joints of the four-joint link mechanism FL. The fourth rotating joint J4 is coupled to the four-joint link mechanism FL and the serial link mechanism SL.

The serial link mechanism SL couples the four-joint link mechanism FL and the movable plate 140 with four degrees of freedom. In the parallel link device 110 related to this embodiment, the serial link mechanism SL includes a fifth link 155 coupled to the portion 157b of the fourth link 157 via the fourth rotating joint J4 and a rotating joint with three degrees of freedom which is connected to a distal end side of the fifth link 155. The rotating joint with three degrees of freedom is constituted of a fifth rotating joint $J_5$, a sixth rotating joint $J_6$, and a seventh rotating joint $J_7$ serving as uniaxially rotated joints. The axes of rotation of the fourth rotating joint $J_4$, the fifth rotating joint $J_5$, the sixth rotating joint $J_6$, and the seventh rotating joint $J_7$ are orthogonal to each other. Although the axes of rotation of the fourth rotating joint $J_4$, the fifth rotating joint $J_5$, and the sixth rotating joint $J_6$ among them are not necessarily orthogonal to each other, the axes of rotation thereof are preferably orthogonal to each other in terms of a structure design or control calculation.

The fifth link 155 is coupled to a sixth link 153 through the fifth rotating joint $J_5$ and the sixth link 153 is coupled to a seventh link 151 through the sixth rotating joint $J_6$. The sixth link 153 and the seventh link 151 may be L-shaped right angle links. The sixth link 153 and the seventh link 151 may have two surfaces orthogonal to each other. In addition, shapes thereof are not limited to L shapes and may be, for example, T shapes. The seventh link 151 is coupled to the fixed part 141a of the movable plate 140 through the seventh rotating joint $J_7$ serving as a uniaxially rotated joint.

The axis of rotation of the seventh rotating joint $J_7$ is directed in a direction of a central point Q of the movable plate 140. The seventh rotating joint $J_7$ is constituted to intersect an axis ($Ax_0$) when viewed along the axis $Ax_0$ connecting the rotational central point P of the coupling positions between the base plate 130 and a plurality of arm parts 150a, 150b, and 150c to the rotational central point Q of the coupling positions between the movable plate 140 and the plurality of arm parts 150a, 150b, and 150c in a state in which any of the axes of rotation (for example, an axis of rotation $O_8$) of the rotating joints of the four-joint link mechanism FL is parallel to an axis of rotation $O_7$ of the seventh rotating joint $J_7$.

In the parallel link device 110 related to this embodiment, the serial link mechanism SL includes the rotating joint with three degrees of freedom at a distal end side to which the movable plate 140 is coupled, an increase in size of the entire device is minimized, and interference with the links, the movable plate 140, and the like hardly occurs. Note that the fifth rotating joint $J_5$ and the sixth rotating joint $J_6$ may be constituted using biaxial rotating joints. Alternatively, the sixth rotating joint $J_6$ and the seventh rotating joint $J_7$ may be constituted using biaxial rotating joints.

The four-joint link mechanism FL is coupled to the movable plate 140 through the serial link mechanism SL with four degrees of freedom. Furthermore, as described above, the fourth link 157 of the four-joint link mechanism FL to which the serial link mechanism SL is coupled can be controlled through the first motor and the second motor with two degrees of freedom. For this reason, the first arm part 150a has an arm structure with six degrees of freedom.

Also, each of the second arm part 150b and the third arm part 150c includes a four-joint link mechanism FL to which first to fourth links 157, 159, 161, and 163 are coupled and a serial link mechanism SL to which fifth to seventh links 151, 153, and 155 are coupled and have the same configuration as the first arm part 150a. The second arm part 150b and the third arm part 150c can also be controlled through two motors with six degrees of freedom.

In other words, the movable plate 140 is supported by the first arm part 150a, the second arm part 150b, and the third arm part 150c which have six degrees of freedom and can perform translational motions with three degrees of freedom and rotational motions with three degrees of freedom. For this reason, the parallel link device 110 can freely change a three-dimensional position and a three-dimensional posture of the movable plate 140 inside a space, where the position and posture corresponds to a location and orientation or configuration of the movable plate 140 in three-dimensional space. The parallel link device 110 with such a configuration is constituted such that the seventh rotating joint $J_7$ intersects the axis ($Ax_0$) when viewed along the axis $Ax_0$ connecting the rotational central point P of the coupling positions among the base plate 130 and the plurality of arm parts 150a, 150b, and 150c to the rotational central point Q of the coupling positions among the movable plate 140 and the plurality of arm parts 150a, 150b, and 150c in a state in which any of the axes of rotation (for example, the axis of rotation $O_8$) of the rotating joints of the four-joint link mechanism FL is parallel to an axis of rotation $O_7$ of the seventh rotating joint $J_7$. In the parallel link device 110 related to this embodiment, the axis of rotation $O_7$ of the seventh rotating joint $J_7$ of the three arm parts 150a, 150b, and 150c intersect at (or is adjacent to) the rotational central point Q of the movable plate 140.

For this reason, ranges of motion of translational motions with three degrees of freedom as well as ranges of motion of rotational motions with three degrees of freedom increase and thus a range of motion of the movable plate 140 is enlarged as compared with a parallel link device in the related art. For example, the parallel link device 110 can accomplish rotational motions having three degrees of freedom with ranges of motion of about ±90 degrees. Ranges of rotational motion of ±90 degrees correspond to ranges of motion of a human wrist.

Also, in the parallel link device 110 related to this embodiment, a total of six motors configured to control postures of the first arm part 150a, the second arm part 150b, and the third arm part 150c can be provided on the base plate 130. For this reason, the parallel link device 110 can be constituted such that weights of the motors thereof are not driven by the motors.

In the parallel link device 110, the motors are provided on the base plate 130, the four-joint link mechanism FL is coupled to the base plate 130, and the serial link mechanism SL is coupled to the distal end side of the four-joint link mechanism FL. For this reason, inertia of the distal end side of the parallel link device 110 is small and this is advantageous in controlling of a three-dimensional position or controlling of a three-dimensional posture of the movable plate 140.

<1-2. Specific Configuration Example of Parallel Link Device>

Next, a specific configuration example of a parallel link device 10 related to this embodiment will be described with reference to FIGS. 3 to 6. FIG. 3 is a perspective view of the parallel link device 10 related to this embodiment and FIG. 4 is a side view of the parallel link device 10. Furthermore, FIG. 5 is a plan view of the parallel link device 10 when viewed from a movable member 40 side and FIG. 6 is a plan view of the parallel link device 10 when viewed from a side of base parts 80a, 80b, and 80c.

The parallel link device 10 includes three groups such as a group of the base part 80a, a movable member 40, a first arm part 50a serving as one among a plurality of arm parts, and a pair of a first motor 91 and a second motor 93 configured to control a posture of the first arm part 50a, a group of the base part 80b, the movable member 40, a second arm part 50b serving as one among the plurality of arm parts, and a pair of a first motor 91 and a second motor 93 configured to control a posture of the second arm part 50b, and a group of the base part 80c, the movable member 40, a third arm part 50c serving as one among the plurality of arm parts, and a pair of a first motor 91 and a second motor 93 configured to control a posture of the third arm part 50c.

The base parts 80a, 80b, and 80c are provided to correspond to the first arm part 50a, the second arm part 50b, and the third arm part 50c, respectively. The base part 80a supports the first arm part 50a, the base part 80b supports the second arm part 50b, and the base part 80c supports the third arm part 50c. The three base parts 80a, 80b, and 80c are disposed around a rotational central point of the three base parts 80a, 80b, and 80c at equal intervals every 120 degrees. The base parts 80a, 80b, and 80c are immovable parts, positions and postures of which do not change along with driving of the first motors 91 and the second motors 93, and a mutual positional relationship between them does not change. For example, the base parts 80a, 80b, and 80c may be fixed to a supporting table or the like (not shown) or the base parts 80a, 80b, and 80c may be coupled to each other.

The movable member 40 may have a hexagonal planar shape to minimize interference with the first arm part 50a, the second arm part 50b, and the third arm part 50c and facilitate control of three-dimensional positions and three-dimensional postures thereof. Furthermore, jigs or the like configured to use the parallel link device 10 can be fixed to the movable member 40, for example, as robotic hands, medical instruments, various haptic presentation devices, controllers, or simulators, or the like. Therefore, any movable member 40 which can support the jigs or the like may be used and a configuration of the movable member 40 is not particularly limited. The jigs or the like are able to be fixed using, for example, bolts, rivets, or the like or a part of the jigs themselves may be set to a predetermined shape corresponding to the movable member 40 and thus the jigs or the like are able to be coupled to distal ends of the arm parts.

In the parallel link device 10 related to this embodiment, the first arm part 50a, the second arm part 50b, and the third arm part 50c have the same configuration. Furthermore, the three base parts 80a, 80b, and 80c also have the same configuration. Hereinafter, a configuration example of arm parts and base parts will be described in detail using the first arm part 50a and the base part 80a as examples.

FIG. 7 is a perspective view showing the first arm part 50a configured to couple the base part 80a and the movable member 40. The first arm part 50a includes a four-joint link mechanism FL which is coupled to the base part 80a and a serial link mechanism SL, a proximal end side of which is coupled to the four-joint link mechanism FL, and a distal end side of which is coupled to the movable member 40. The four-joint link mechanism FL is constituted of a first link 59, a second link 63, a third link 61, and a fourth link 57. Furthermore, the serial link mechanism SL is constituted of a fifth link 55, a sixth link 53, and a seventh link 51. The links may be formed using various materials such as, for example, aluminum, stainless steel, and a resinous material.

A constituent material may be selected by regarding lightness thereof as important and may be selected by regarding manufacturing costs as important.

A posture of the first arm part 50a is controlled using the first motor 91 and the second motor 93. The first motor 91 and the second motor 93 are fixed to the base part 80a. An axis of rotation $Ax_1$ of an output shaft 71 of the first motor 91 and an axis of rotation $Ax_2$ of an output shaft 75 of the second motor 93 are disposed to be parallel to each other. The first motor 91 rotates the first link 59 about a first active joint $J_8$. Rotation of the first motor 91 is transferred to the first active joint $J_8$ via a first speed reduction mechanism $SR_1$. The first active joint $J_8$ is rotatably supported by the base part 80a via a bearing or the like.

The base part 80a rotates the second link 63 about a second active joint $J_9$. Rotation of the second motor 93 is transferred to the second active joint $J_9$ via a second speed reduction mechanism $SR_2$. In the parallel link device 10 related to this embodiment, the second link 63 is constituted by a part of the second speed reduction mechanism $SR_2$. The second active joint $J_9$ is rotatably supported by the base part 80a via a bearing or the like. An axis of rotation $O_9$ of the second active joint $J_9$ and an axis of rotation $O_8$ of the first active joint $J_8$ are disposed to be coaxial with each other. Here, the axis of rotation $O_9$ of the second active joint $J_9$ and the axis of rotation $O_8$ of the first active joint $J_8$ may not be disposed to be coaxial with each other as long as the axis of rotation $O_9$ thereof and the axis of rotation $O_8$ thereof are parallel to each other.

Here, one configuration example of the first speed reduction mechanism $SR_1$ and the second speed reduction mechanism $SR_2$ will be described with reference to FIGS. 8 and 9. The first speed reduction mechanism $SR_1$ and the second speed reduction mechanism $SR_2$ may have the same configuration. In addition, here, description is provided using the second speed reduction mechanism $SR_2$ as an example. FIG. 8 is a schematic diagram of the second speed reduction mechanism $SR_2$ when viewed along an axis of rotation $Ax_2$ of the output shaft 75 of the second motor 93 and FIG. 9 is a schematic diagram of a part of the second speed reduction mechanism $SR_2$ when viewed in a direction orthogonal to an axis of rotation $Ax_2$ of the output shaft 75 of the second motor 93.

Such a second speed reduction mechanism $SR_2$ is a speed reduction mechanism using a wire 79 as a rotation transferring member. A spiral groove 75a around which the wire 79 is wound is provided in a part of an outer peripheral surface of the output shaft 75 of the second motor 93. Both end sides of the wire 79 wound around the output shaft 75 are arranged along an outer peripheral surface 77a of a rotating member 77 supported by the base part 80a to be able to rotate through the second active joint $J_9$. Both end sides of the wire 79 are fixed to the rotating member 77 and a predetermined tension is applied to the wire 79.

The rotating member 77 has a substantially fan-shaped planar shape about the axis of rotation $O_9$ of the second active joint $J_9$. The outer peripheral surface 77a of the rotating member 77 has a circular arc shape about the axis of rotation $O_9$ of the second active joint $J_9$. A diameter of a circular arc formed by the outer peripheral surface 77a of the rotating member 77 is larger than a winding diameter of the wire 79 in the output shaft 75 of the second motor 93. A second rotating joint $J_2$ to which the third link 61 is coupled is provided on an outer circumference side of the rotating member 77. The rotating member 77 also functions as the second link 63 of the four-joint link mechanism FL.

In the second speed reduction mechanism $SR_2$, if the second motor 93 is rotatably driven, one end side of the wire 79 wound around the output shaft 75 is wound around the output shaft 75 and the other end side thereof is led out from the output shaft 75. The rotating member 77 to which both ends of the wire 79 are fixed rotates in a direction opposite to a rotational direction of the output shaft 75 about the second active joint $J_9$ along with such winding and leading out of the wire 79. Thus, the second link 63 is rotated about the second active joint $J_9$ by the second motor 93.

At this time, the diameter of the circular arc formed by the outer peripheral surface 77a of the rotating member 77 is larger than the winding diameter of the wire 79 in the output shaft 75 of the second motor 93. Thus, rotation of the second motor 93 decelerates and is transferred to the rotating member 77. When the winding diameter of the wire 79 in the output shaft 75 of the second motor 93 is set to R1 and the diameter of the circular arc formed by the outer peripheral surface 77a of the rotating member 77 is set to R2, a speed reduction ratio is R1/R2. The second speed reduction mechanism $SR_2$ using the wire 79 is set as a rotation transferring member so that back drivability increases and backlash decreases as compared with a case in which a speed reduction gear is used.

Referring again to FIG. 7, the first link 59 is coupled to the fourth link 57 through a first rotating joint $J_1$. Furthermore, the second link 63 is coupled to the third link 61 through the second rotating joint $J_2$ and the third link 61 is coupled to the fourth link 57 through a third rotating joint $J_3$. The four-joint link mechanism FL is constituted such that the axis of rotation $O_8$ of the first active joint $J_8$, an axis of rotation $O_1$ of the first rotating joint $J_1$, an axis of rotation $O_2$ of the second rotating joint $J_2$, and an axis of rotation $O_3$ of the third rotating joint $J_3$ are disposed to be parallel to each other. Therefore, the first motor 91 and the second motor 93 are driven so that the fourth link 57 is controlled with two degrees of freedom. The four-joint link mechanism FL is constituted as a parallel link mechanism.

The fourth link 57 has a substantially L shape. A fourth rotating joint $J_4$ is provided on a portion 57b rising vertically from a portion 57a of the fourth link 57 on which the first rotating joint $J_1$ and the third rotating joint $J_3$ are provided. An axis of rotation $O_4$ of the fourth rotating joint $J_4$ is orthogonal to the axes of rotation of the rotating joints of the four-joint link mechanism FL. The four-joint link mechanism FL is coupled to the serial link mechanism SL through the fourth rotating joint $J_4$.

The serial link mechanism SL includes the fifth link 55 coupled to the fourth link 57 through the fourth rotating joint $J_4$ and is coupled to the movable member 40 via a rotating joint with three degrees of freedom provided on the distal end side of the fifth link 55. The rotating joint with three degrees of freedom is constituted of a fifth rotating joint $J_5$ configured to couple the fifth link 55 and the sixth link 53, a sixth rotating joint $J_6$ configured to couple the sixth link 53 and the seventh link 51, and a seventh rotating joint $J_7$ configured to couple the seventh link 51 and the movable member 40. The axis of rotation $O_4$ of the fourth rotating joint $J_4$, an axis of rotation $O_5$ of the fifth rotating joint $J_5$, an axis of rotation $O_6$ of the sixth rotating joint $J_6$, and an axis of rotation $O_7$ of the seventh rotating joint $J_7$ are disposed to be orthogonal to each other.

In other words, the four-joint link mechanism FL is coupled to the movable member 40 through the serial link mechanism SL with four degrees of freedom. As described above, the first arm part 50a has an arm structure with six degrees of freedom. The serial link mechanism SL includes the rotating joint with three degrees of freedom on the distal end side of the fifth link 55. For this reason, an increase in size of the parallel link device 10 is minimized, interference of the links, the movable member 40, and the like is suppressed, and thus a wide range of motion of the movable member 40 can be secured.

As described above, the fifth rotating joint $J_5$ and the sixth rotating joint $J_6$ may be constituted using a biaxial rotating joint. Alternatively, the sixth rotating joint $J_6$ and the seventh rotating joint $J_7$ may be constituted using a biaxial rotating joint. The number of links can be reduced using a biaxial rotating joint.

The second arm part 50b and the third arm part 50c also have arm structures with six degrees of freedom as in the first arm part 50a and postures of the arm parts are controlled using a pair of a first motor 91 and a second motor 93. In other words, the movable member 40 is supported by the three arm parts with six degrees of freedom and can perform translational motions with three degrees of freedom and rotational motions with three degrees of freedom. Thus, the parallel link device 10 can freely change a three-dimensional position and a three-dimensional posture of the movable member 40.

Note that, in the parallel link device 10 shown in FIGS. 3 to 6, the movable member 40 is located at substantially intermediate positions in ranges of motion of the translational motions with three degrees of freedom and the rotational motions with three degrees of freedom. Hereinafter, a position of the movable member 40 in such a state is referred to as "a standard position" and a posture of the movable member 40 is referred to as "a standard posture." When the movable member 40 is in the standard position and the standard posture, the first arm part 50a, the second arm part 50b, and the third arm part 50c are twisted in the same direction. In the parallel link device 10 related to this embodiment, when the movable member 40 is in the standard position and the standard posture, the first arm part 50a, the second arm part 50b, and the third arm part 50c are twisted in a counterclockwise direction. In the parallel link device 10, a twisted direction thereof may be reversed.

<1-3. Motion of Parallel Link Device>

Next, an operation of the parallel link device 10 related to this embodiment will be described. FIGS. 10 to 15 illustrate states in which three-dimensional postures of the movable member 40 are changed in accordance with a change in postures of the first arm part 50a, the second arm part 50b, and the third arm part 50c of the parallel link device 10. In FIGS. 10 to 15, the movable member 40 in the standard position and the standard posture shown in FIG. 3 is indicated using an alternate long and two short dashed lines.

Note that, in the following description, virtual surfaces on which bottom surfaces of the three base parts 80a, 80b, and 80c are placed (surfaces parallel to the bottom surfaces of the three base parts 80a, 80b, and 80c) are referred to as "placing surfaces." Furthermore, in order to facilitate understanding, rotation around a z axis extending in a forward and rearward direction of the parallel link device 10 in the standard posture shown in FIG. 3 is referred to as roll rotation, rotation along the axis of rotation $O_7$ of the seventh rotating joint $J_7$ of the first arm part 50a of the parallel link device 10 in the standard posture shown in FIG. 3 and around an x axis orthogonal to the z axis is referred to as yaw rotation, and rotation around a y axis orthogonal to the x axis and the z axis is referred to as pitch rotation.

Also, in the following description, a rotational direction of the first motor 91 and the second motor 93 is a rotational direction when they are viewed in a direction along which output shafts thereof extend from a motor main body.

(1-3-1. Roll Rotation)

Roll rotation of the parallel link device 10 related to this embodiment will be described. FIG. 10 illustrates a state of the parallel link device 10 when the first motors 91 and the second motors 93 of the first arm part 50a, the second arm part 50b, and the third arm part 50c are rotatably driven in a clockwise direction from the state in FIG. 3. In this case, the first links 59 and the second links 63 of the arm parts 50a, 50b, and 50c rotate about the first active joint $J_8$ and the second active joint $J_9$ to rise from the placing surface.

Thus, fixed parts 41a, 41b, and 41c of the movable member 40 to which the distal end sides of the arm parts 50a, 50b, and 50c are coupled rotate about the z axis in an arrow $Dz_1$ direction while positions thereof in a z axis direction are substantially maintained. As a result, the movable member 40 coupled to and supported by the distal end sides of the three arm parts 50a, 50b, and 50c rotates in a roll manner in the arrow $Dz_1$ direction about the z axis while maintaining a three-dimensional position thereof.

Also, FIG. 11 illustrates a state of the parallel link device 10 when the first motors 91 and the second motors 93 of the first arm part 50a, the second arm part 50b, and the third arm part 50c are rotatably driven in a counterclockwise direction from the state in FIG. 3. In this case, the first links 59 and the second links 63 of the arm parts 50a, 50b, and 50c rotate about the first active joint $J_8$ and the second active joint $J_9$ to approach the placing surface.

Thus, the fixed parts 41a, 41b, and 41c of the movable member 40 to which the distal end sides of the arm parts 50a, 50b, and 50c are coupled rotate about the z axis in an arrow $Dz_2$ direction opposite to the arrow $Dz_1$ direction while the positions thereof in the z axis direction are substantially maintained. Therefore, the movable member 40 coupled to and supported by the distal end sides of the three arm parts 50a, 50b, and 50c rotate about the z axis in a roll manner in the arrow $Dz_2$ direction opposite to the arrow $Dz_1$ direction while maintaining a three-dimensional position thereof.

As shown in FIGS. 10 and 11, in the parallel link device 10 related to this embodiment, a range of motion of a roll rotating motion of the movable member 40 about the z axis is about 90 degrees.

(1-3-2. Yaw rotation)

Next, yaw rotation of the parallel link device 10 related to this embodiment will be described. FIG. 12 illustrates a state of the parallel link device 10 when the first motor 91 of the second arm part 50b is rotatably driven in a clockwise direction and the second motor 93 is rotatably driven in a counterclockwise direction and the first motor 91 of the third arm part 50c is rotatably driven in a counterclockwise direction and the second motor 93 is rotatably driven in a clockwise direction while a posture of the first arm part 50a is maintained as in the state in FIG. 3. In this case, the first link 59 of the second arm part 50b rotates about the first active joint $J_8$ to rise from the placing surface and the second link 63 rotates about the second active joint $J_9$ to approach the placing surface. Thus, the fixed part 41b of the movable member 40 to which the distal end side of the second arm part 50b is coupled rotates about the x axis toward a front side of the z axis.

Also, the first link 59 of the third arm part 50c rotates about the first active joint $J_8$ to approach the placing surface and the second link 63 thereof rotates about the second active joint $J_9$ to rise from the placing surface. Thus, the fixed part 41c of the movable member 40 to which the distal end side of the third arm part 50c is coupled rotates about the x axis toward the rear side of the z axis. As a result, the movable member 40 coupled to and supported by the distal end sides of the three arm parts 50a, 50b, and 50c rotates about the x axis in a yaw manner in an arrow $Dx_1$ direction while maintaining a three-dimensional position thereof.

FIG. 13 illustrates a state of the parallel link device 10 when the first motor 91 of the second arm part 50b is rotatably driven in a counterclockwise direction and the second motor 93 thereof is rotatably driven in a clockwise direction and the first motor 91 of the third arm part 50c is rotatably driven in a clockwise direction and the second motor 93 thereof is rotatably driven in a counterclockwise direction while a posture of the first arm part 50a is maintained as in the state in FIG. 3. In this case, the first link 59 of the second arm part 50b rotates about the first active joint $J_8$ to approach the placing surface and the second link 63 thereof rotates about the second active joint $J_9$ to rise from the placing surface. Thus, the fixed part 41b of the movable member 40 to which the distal end side of the second arm part 50b is coupled rotates about the x axis toward the front side of the z axis.

Also, the first link 59 of the third arm part 50c rotates about the first active joint $J_8$ to rise from the placing surface and the second link 63 thereof rotates about the second active joint $J_9$ to approach the placing surface. Thus, the fixed part 41c of the movable member 40 to which the distal end side of the third arm part 50c is coupled rotates about the x axis toward the front side of the z axis. As a result, the movable member 40 coupled to and supported by the distal end sides of the three arm parts 50a, 50b, and 50c rotates about the x axis in a yaw manner in an arrow $Dx_2$ direction opposite to the arrow $Dx_1$ direction while maintaining a three-dimensional position thereof.

As shown in FIGS. 12 and 13, in the parallel link device 10 related to this embodiment, a range of motion of a yaw rotating motion of the movable member 40 about the x axis is about 90 degrees.

(1-3-3. Pitch Rotation)

Next, pitch rotation of the parallel link device 10 related to this embodiment will be described. FIG. 14 illustrates a state of the parallel link device 10 when the first motor 91 of the first arm part 50a is rotatably driven in a clockwise direction and the second motor 93 thereof is rotatably driven in a counterclockwise direction, the first motor 91 of the second arm part 50b is rotatably driven in a counterclockwise direction and the second motor 93 thereof is rotatably driven in a clockwise direction, and the second motor 93 of the third arm part 50c is rotatably driven in a clockwise direction from the state in FIG. 3. In this case, the first link 59 of the first arm part 50a rotates about the first active joint $J_8$ to rise from the placing surface and the second link 63 thereof rotates about the second active joint $J_9$ to approach the placing surface. Thus, the fixed part 41a of the movable member 40 to which the distal end side of the first arm part 50a is coupled rotates about the y axis toward the front side of the z axis.

Also, the first link 59 of the second arm part 50b rotates about the first active joint $J_8$ to approach the placing surface and the second link 63 thereof rotates about the second active joint $J_9$ to rise from the placing surface. Thus, the fixed part 41b of the movable member 40 to which the distal end side of the second arm part 50b is coupled rotates about the y axis toward the front side of the z axis. Furthermore, the second link 63 rotates about the second active joint $J_9$ to rise from the placing surface while a posture of the first link 59 of the third arm part 50c is maintained. Thus, the fixed part 41c of the movable member 40 to which the distal end side of the third arm part 50c is coupled rotates about the y axis toward the rear side of the z axis. As a result, the movable member 40 coupled to and supported by the distal end sides of the three arm parts 50a, 50b, and 50c rotates about the y axis in a pitch manner in an arrow $Dy_1$ direction while maintaining a three-dimensional position thereof.

FIG. 15 illustrates a state of the parallel link device 10 when the first motor 91 of the first arm part 50a is rotatably driven in a counterclockwise direction and the second motor 93 thereof is rotatably driven in a clockwise direction, the first motor 91 of the second arm part 50b is rotatably driven in a clockwise direction and the second motor 93 is rotatably driven in a counterclockwise direction, and the second motor 93 of the third arm part 50c is rotatably driven in a counterclockwise direction from the state in FIG. 3. In this case, the first link 59 of the first arm part 50a rotates about the first active joint $J_8$ to approach the placing surface and the second link 63 thereof rotates about the second active joint $J_9$ to rise from the placing surface. Thus, the fixed part 41a of the movable member 40 to which the distal end side of the first arm part 50a is coupled rotates about the y axis toward the rear side of the z axis.

Also, the first link 59 of the second arm part 50b rotates about the first active joint $J_8$ to rise from the placing surface and the second link 63 rotates about the second active joint $J_9$ to approach the placing surface. Thus, the fixed part 41b of the movable member 40 to which the distal end side of the second arm part 50b is coupled rotates about the y axis in an arrow $Dy_2$ direction while moving toward the front side of the z axis. Furthermore, the second link 63 rotates about the second active joint $J_9$ to approach the placing surface while a posture of the first link 59 of the third arm part 50c is maintained. Thus, the fixed part 41c of the movable member 40 to which the distal end side of the third arm part 50c is coupled rotates about the y axis toward the front side of the z axis. As a result, the movable member 40 coupled to and supported by the distal end sides of the three arm parts 50a, 50b, and 50c rotates about the y axis in a pitch manner in the arrow $Dy_2$ direction opposite to the arrow $Dy_1$ direction while maintaining a three-dimensional position thereof.

As shown in FIGS. 14 and 15, in the parallel link device 10 related to this embodiment, a range of motion of a pitch rotating motion of the movable member 40 about the y axis is about 90 degrees.

(1-3-4. Six Degrees of Freedom Motion)

Although not illustrated in the drawing, in the parallel link device 10, a total of six motors configured to control the first arm part 50a, the second arm part 50b, and the third arm part 50c are controlled so that a three-dimensional position of the movable member 40 on the x axis, the y axis, and the z axis can be changed from the state of the standard position shown in FIG. 3. In other words, in the parallel link device 10, rotation angles of the motors are appropriately set so that translational motions with three degrees of freedom and rotational motions with three degrees of freedom of the movable member 40 are possible and thus the three-dimensional position and the three-dimensional posture can be freely changed.

At this time, the parallel link device 10 related to this embodiment is constituted such that the axis of rotation $O_7$ of the seventh rotating joint $J_7$ of the distal end sides of the three arm parts 50a, 50b, and 50c coupled to the movable member 40 passes through a rotational central point Q. The axis of rotation $O_7$ of the seventh rotating joint $J_7$ intersects an axis $Ax_0$ when viewed along the axis $Ax_0$ connecting a rotational central point P of coupling positions among the base parts 80*a*, 80*b*, and 80*c* and the plurality of arm parts 50*a*, 50*b*, and 50*c* to the rotational central point Q of coupling positions among the movable member 40 and the plurality of arm parts 50*a*, 50*b*, and 50*c* in a state in which any of axes of rotation (for example, an axis of rotation $O_1$) of rotating joints of a four-joint link mechanism is parallel to the axis of rotation $O_7$ of the seventh rotating joint $J_7$ (for example, refer to FIG. 5). For this reason, ranges of motion of yaw rotation, pitch rotation, and roll rotation about the x axis, the y axis, and the z axis can be secured at about 90 degrees.

Although ranges of motion of rotational motions with three degrees of freedom can be limited due to interference between the links, the movable member 40, and the base parts 80*a*, 80*b*, and 80*c*, according to the parallel link device 10 related to this embodiment, the ranges of motion of the rotational motions can be set at, at least 80 degrees or more. In order to minimize such interference and secure larger ranges of motion of rotational motions of the movable member 40, for example, it is advantageous that the links are thinner links. Furthermore, the links may have a shape such an L shape or a U shape rather than a linear shape to minimize such interference. In order to minimize interference between the links and the movable member 40, the movable member 40 may have a hexagonal shape.

As described above, in the parallel link device 10 related to this embodiment, ranges of motion of rotational motions with three degrees of freedom of roll rotation, yaw rotation, and pitch rotation as well as ranges of motion of translational motions with three degrees of freedom are enlarged and thus a three-dimensional position and a three-dimensional posture thereof can be freely changed.

On the other hand, if ranges of motion of rotating joints of the arm parts 50*a*, 50*b*, and 50*c* are unlimited, there is a concern in that at least one of the arm parts 50*a*, 50*b*, and 50*c* may become caught in a singular point. For this reason, stoppers used to restrict ranges of motion may be provided in all rotating joints such that ranges of motion of the arm parts 50*a*, 50*b*, and 50*c* are limited.

<1-4. Usage Modes of Parallel Link Device>

The parallel link device 10 related to this embodiment can be used for the purpose of various applications. For example, the parallel link device 10 may be applied to industrial robots used in manufacturing devices, production lines, and the like. Furthermore, the parallel link device 10 may be applied to medical robots such as manipulators configured to support surgical tools such as an endoscope, an electron microscope, and a forceps. The parallel link device 10 is connected to various external devices in a wired or wireless manner and may be applied to an input device, a controller, or a simulator which remotely control the external devices.

Also, the parallel link device 10 can be installed at an appropriate place depending on applications. For example, the parallel link device 10 may be suspended by fixing the base parts 80*a*, 80*b*, and 80*c* to a ceiling, a beam, or the like and used. The base parts 80*a*, 80*b*, and 80*c* of the parallel link device 10 may be fixed to a floor surface or the like so that the plurality of arm parts 50*a*, 50*b*, and 50*c* may be provided to extend upward. Alternatively, the base parts 80*a*, 80*b*, and 80*c* of the parallel link device 10 may be fixed to a wall surface or the like so that the plurality of arm parts 50*a*, 50*b*, and 50*c* may be installed to extend sideward. For example, when the parallel link device 10 is applied to an input device, a controller, or a simulator, the parallel link device 10 may be installed such that the plurality of arm parts 50*a*, 50*b*, and 50*c* extend upward or sideward.

The parallel link device 10 related to this embodiment can perform translational motions with three degrees of freedom and rotational motions with three degrees of freedom having wide ranges of motion. Thus, the parallel link device 10 can be effectively used while freely changing a three-dimensional position and a three-dimensional posture in any application.

For example, when the parallel link device 10 is applied to industrial robots, medical manipulators, and the like, a control device having a microcomputer such as a central processing unit (CPU) is included in the parallel link device 10. Such a control device can be constituted to receive a manipulation input transmitted from an appropriate manipulation input device, calculate amounts of control of six motors, and output a control instruction to the motors.

A manipulation input device is provided, for example, at a position away from the parallel link device 10 and receives an input of an instruction on an operation of the parallel link device 10 by a user (including a surgeon or an assistant). The manipulation input device can include, for example, a manipulation button configured to provide an instruction for a forward, rearward, leftward or rightward motion, a manipulation button configured to provide an instruction for a vertical motion, and a manipulation portion configured to provide an instruction for a rotational motion. Alternatively, the manipulation input device may be a device obtained through a combination of a device which can provide an instruction for an inclination in directions over 360° such as a joystick and an input device configured to provide an instruction for a vertical motion or a rotational motion. Furthermore, the manipulation input device may be a touch panel or the like.

Also, the manipulation input device may be integrated with a manipulation part configured to manipulate a jig of a robotic hand, an endoscope, an end effector, or the like supported by the movable member 40 of the parallel link device 10. The manipulation input device configured to manipulate the parallel link device 10 is integrated with the manipulation part of the jig so that the user can change a position and a posture of the movable member 40 while the user himself or herself manipulates the jig even if there is no assistant. Note that communication between the manipulation input device and the control device can be performed through various known wired or wireless methods.

The control device controls a three-dimensional position and a three-dimensional posture of a jig supported by the movable member 40, for example, by controlling rotation angles of motors. The control device may be, for example, a processor such as a CPU or a digital signal processor (DSP). Alternatively, the control device may be a control board or a microcomputer on which storage elements such as a processor and a memory are mounted. A processor constituting the control device executes various signal processes in accordance with a predetermined program so that translational motions with three degrees of freedom and rotational motions with three degrees of freedom of various jigs or the like supported by the movable member 40 are performed.

Also, the parallel link device 10 may be controlled on the basis of forward kinematics and controlled on the basis of inverse kinematics. When the parallel link device 10 is controlled on the basis of forward kinematics, three-dimensional positions and three-dimensional postures of various jigs or the like supported by the movable member 40 can be obtained from rotation angles of six motors. Furthermore, when the parallel link device 10 is controlled on the basis of inverse kinematics, instruction values of the rotation angles of the six motors can be obtained in accordance with a desired three-dimensional position and three-dimensional posture of a jig or the like. In this case, the control device may control the rotation angles of the motors so that rotation angles of the motors which can be detected, for example, using a potentiometer or the like are calculated instruction values.

As described above, when the parallel link device 10 is controlled by the control device, a range of motion of any of yaw rotation, roll rotation, and pitch rotation of the movable member 40 is also about ±90 degrees. For this reason, in various robots or the like to which the parallel link device 10 is applied, three-dimensional positions and three-dimensional postures of various jigs or the like supported by the movable member 40 can be freely controlled in accordance with a range of motion of a human wrist.

<1-5. Application Examples>

Next, several application examples of a parallel link robot to which the parallel link device 10 related to this embodiment is applied will be described.

(1-5-1. Lock Function)

A parallel link robot may have a lock function configured to hold postures of the plurality of arm parts 50a, 50b, and 50c in predetermined postures. For example, when the user manually moves the movable member 40, and determines a position and a posture of the movable member 40, and rotation torques are applied to the first motor 91 and the second motor 93 due to an external force, a torque against the external force may be generated by supplying a current to the motors through the control device or the like. Thus, the motors can hold the original positions and postures. Such a lock function can be realized as a servo lock function, for example, when servo motors are used as the motors. In this case, the rotation torques applied due to an external force can be detected on the basis of, for example, pulse signals flowing through the servo motors.

The lock function may be started when the user turns on setting of the lock function or may be automatically started when rotation of the first motor 91 and the second motor 93 stops for several seconds (for example, for three seconds). Furthermore, the lock function may be released when the user turns off the setting of the lock function or may be released when rotation torques are continuously applied to the first motor 91 and the second motor 93 for several seconds or more (for example, for three seconds or more) due to an external force. The lock function may be released when a manipulation instruction of the plurality of arm parts 50a, 50b, and 50c is input to the manipulation input device.

(1-5-2. Assist Function)

The parallel link robot may have an assist function configured to apply an assisting force to manipulation of the plurality of arm parts 50a, 50b, and 50c by the user. For example, when the user manually moves the movable member 40, if the control device detects that rotation torques have been applied to the first motor 91 and the second motor 93, a torque in the same direction as an external force may be generated by supplying a current to the motors. At this time, a ratio between torques applied to the motors may coincide with a ratio between rotation torques applied to the motors. Thus, the movable member 40 can be moved in a direction of operation desired by the user.

(1-5-3. Haptic Presentation Function)

The parallel link robot may be used as a haptic presentation device with a haptic presentation function used to present a shape, hardness, a reaction force, and the like to the user. For example, a position of an object to be manipulated may be moved inside a virtual space in which an image is displayed on the basis of torques by detecting, by the control device, torques received by the motors when the user has moved the movable member 40 while viewing the image. At this time, when the object to be manipulated comes into contact with a surface or the like of a predetermined virtual object, resistance may be applied to rotation of the motors against a direction of a translational motion or a rotational motion of the movable member 40 so that hardness of the virtual object may be presented. Alternatively, when the object to be manipulated moving inside the virtual space comes into contact with a surface or the like of a predetermined virtual object, vibrations may be applied to the movable member 40 through a vibration generating element or the like so that a tactile sense of the virtual object may be presented.

Specific examples of the parallel link robot with such a haptic presentation function include an example in which the parallel link device 10 is applied to a controller of a surgical simulator. In such an example, information on a position, a shape, and the like of a skeleton or the like around an affected area of a patient to be operated on is obtained in advance, and the user moves the movable member 40 while viewing a virtual image displayed on a monitor or the like. At this time, when a surgical tool inside the virtual space comes into contact with the patient's body or the like, force detection presentation may be performed through the control device.

Particularly, the parallel link robot may be used as an input device at a master side for bilateral control which presents a force received by a slave-side device to be remotely manipulated to the user (the master side) or presents a force to the slave-side device in accordance with a force input by the user. For example, the parallel link robot can be used as an input interface of a surgical navigation device. In such an example, information on a position, a shape, and the like of a skeleton or the like around an affected area of a patient to be operated on is obtained in advance, and the user manipulates the movable member 40 while viewing imaging information displayed on a monitor. At this time, torques received by the motors are detected through the control device and a position and a posture of a real surgical tool supported by the slave-side device can be controlled on the basis of the torques. Furthermore, when the real surgical tool supported by the slave-side device comes into contact with the patient's body, the control device controls outputs of the motors on the basis of a force detected on the slave-side device so that force presentation is performed for the user.

In the parallel link device related to this embodiment, a three-dimensional posture of the movable member can be freely changed while a center of rotational motions with three degrees of freedom is fixed to one point. Furthermore, when the parallel link device related to this embodiment is applied to a haptic presentation device, free force feedbacks can be performed through control in a transitional direction and a rotational direction. A utilization range of the haptic presentation device can be enlarged.

<1-6. Conclusion>

As described above, in the parallel link device related to this embodiment, the base part and the movable member are supported by a first arm part, a second arm part, and a third arm part in parallel. Each of the arm parts is constituted of a four-joint link mechanism coupled to the base part and a serial link mechanism with four degrees of freedom, a proximal end side of which is coupled to the four-joint link mechanism and a distal end side of which is coupled to the movable member. In other words, the base part and the movable member are supported by three arm parts with six degrees of freedom in parallel. Therefore, the movable member can perform translational motions with three degrees of freedom and rotational motions with three degrees of freedom.

Also, in the parallel link device, the axis of rotation $O_7$ of the seventh rotating joint $J_7$ coupled to the movable member of the serial link mechanism is directed in a direction of the rotational central point Q of the movable member. The axis of rotation $O_7$ of the seventh rotating joint $J_7$ intersects the axis $Ax_0$ when viewed along the axis $Ax_0$ connecting the rotational central point P of the coupling positions among the base parts 80a, 80b, and 80c and the plurality of arm parts 50a, 50b, and 50c to the rotational central point Q of the coupling positions among the movable member 40 and the plurality of arm parts 50a, 50b, and 50c in a state in which any of the axes of rotation (for example, an axis of rotation $O_1$) of the rotating joints of the four-joint link mechanism is parallel to the axis of rotation $O_7$ of the seventh rotating joint $J_7$. For this reason, ranges of motion of rotational motions with three degrees of freedom of the movable member increase and thus a three-dimensional position and a three-dimensional posture thereof can be freely changed.

Also, in the parallel link device related to this embodiment, the first motor and the second motor configured to change postures of the arm parts are supported by the base part. For this reason, since weights of the motors need not be driven through another motor, loads on the motors are reduced. In the parallel link device related to this embodiment, the motors are supported by the base part, the four-joint link mechanism is coupled to the base part, and the serial link mechanism is coupled to the distal end side of the four-joint link mechanism. For this reason, the distal end side of the parallel link device is lightened and thus inertia of the distal end side thereof becomes smaller. Therefore, this is advantageous in controlling a three-dimensional position or controlling a three-dimensional posture of the movable member.

According to the parallel link device related to this embodiment, an input interface in which inertia is small, force presentation is possible, ranges of motion of translational motions with three degrees of freedom and rotational motions with three degrees of freedom are large, and bilateral control can be performed can be obtained.

The parallel link device related to this embodiment can be constituted of six motors, a base part with a relatively simple configuration, and three arm parts. For this reason, a six axis parallel link device in which ranges of motion of translational motions with three degrees of freedom and rotational motions with three degrees of freedom are large and a high speed operation can be performed can be manufactured at low cost.

In the parallel link device related to this embodiment, the first active joint $J_8$ rotating using the first motor and the second active joint $J_9$ rotating using the second motor are disposed to be coaxial with each other. For this reason, a parallel link device in which an arithmetic process used to control a three-dimensional position and a three-dimensional posture of the movable member becomes easy and thus a position or a posture thereof can be accurately controlled can be obtained.

2. Second Embodiment

Next, a parallel link device according to a second embodiment of this disclosure will be described. In the parallel link device related to this embodiment, coupling parts between a plurality of arm parts and a base part are unevenly located around a rotational central point P in a predetermined range. Similarly, in the parallel link device, coupling parts between the plurality of arm parts and a movable member are unevenly located around a rotational central point Q in a predetermined range. Hereinafter, differences between the parallel link device related to this embodiment and the parallel link device related to the first embodiment will be mainly described.

FIG. 16 is an explanatory diagram illustrating a structure of a parallel link device 210 related to this embodiment. In the parallel link device 210 related to this embodiment, fixed parts 231a, 231b, and 231c which are provided on a base plate 230 serving as a base part and to which a first arm part 150a, a second arm part 150b, and a third arm part 150c are coupled are located close to one side around the rotational central point P. The fixed parts 231a, 231b, and 231c are provided around the rotational central point P at equal intervals every 60 degrees. Furthermore, in the parallel link device 210, fixed parts 241a, 241b, and 241c which are provided on a movable plate 240 serving as a movable member and to which the first arm part 150a, the second arm part 150b, and the third arm part 150c are coupled are located close to one side around the rotational central point Q. The fixed parts 241a, 241b, and 241c are provided around the rotational central point P at equal intervals every 60 degrees.

The parallel link device 210 related to this embodiment can have the same configuration as the parallel link device related to the first embodiment but is different from the parallel link device related to the first embodiment in that, in the parallel link device 210 related to this embodiment, disposition of coupling parts between the first arm part 150a, the second arm part 150b, and the third arm part 150c and the fixed parts 231a, 231b, and 231c or the fixed parts 241a, 241b, and 241c is different. Furthermore, although not illustrated in the drawing, various parallel link robots to which the parallel link device 210 related to this embodiment is applied can also have a configuration according to the example of the parallel link robot related to the first embodiment.

In other words, also in the parallel link device 210 related to this embodiment, an axis of rotation $O_7$ of a seventh rotating joint $J_7$ intersects an axis $Ax_0$ when viewed along the axis $Ax_0$ connecting the rotational central point P of coupling positions among the base plate 230 and the plurality of arm parts 150a, 150b, and 150c to the rotational central point Q of coupling positions among the movable plate 240 and the plurality of arm parts 150a, 150b, and 150c in a state in which any of axes of rotation (for example, an axis of rotation $O_8$) of rotating joints of a four-joint link mechanism FL is parallel to the axis of rotation $O_7$ of the seventh rotating joint $J_7$. For this reason, ranges of motion of rotational motions with three degrees of freedom of the movable plate 240 increase and thus a three-dimensional position and a three-dimensional posture thereof can be freely changed.

In the parallel link device 210 related to this embodiment, the fixed parts 231a, 231b, and 231c of the base plate 230 or the fixed parts 241a, 241b, and 241c of the movable plate 240 are disposed every 60 degrees. Thus, when the user grips the movable plate 240, the three arm parts 150a, 150b, and 150c are constituted not to interfere with the user's hands or arms. Therefore, the parallel link device 210 is suitable for being used as an input device or a controller.

FIG. 17 illustrates an example of a usage mode of the parallel link device 210 related to this embodiment. In the example shown in FIG. 17, the base plate 230 of the parallel link device 210 is fixed to a distal end part of an armrest of a chair on which the user sits and the plurality of arm parts 150a, 150b, and 150c extend to a lateral side at which the user is present. Furthermore, the fixed parts 231a, 231b, and 231c unevenly located around the rotational central point P are disposed at a front side when viewed from the user sitting on the chair. For this reason, the user can easily access a stylus type gripping member 201 attached to the movable plate 240 from a space between the first arm part 150a, the second arm part 150b, and the third arm part 150c while sitting on the chair.

In FIG. 17, although an actuator is not illustrated in the drawing, the parallel link device 210 related to this embodiment can also be used as an input device on which bilateral control can be performed as in the parallel link device 10 related to the first embodiment. Furthermore, although a usage mode of the parallel link device 210 manipulated by the user's right hand is illustrated in FIG. 17, the parallel link device 210 may be constituted to be able to be manipulated by both the user's hands using two parallel link devices 210.

When the parallel link device 210 is used as an input device, the movable plate 240 may have a shape in which it is easily gripped by the user. For example, the movable plate 240 may have a thickness of about 5 to 15 mm to be easily sandwiched between the user's fingers. Furthermore, the movable plate 240 may include a receiving part configured to receive the user's finger. The receiving part may be, for example, a hole part 245 illustrated in FIG. 16 or may be a concave portion or a convex portion. The movable plate 240 includes such a receiving part so that the movable plate 240 can be prevented from slipping out of or escaping from the user's hand.

As described above, in the parallel link device related to this embodiment, the fixed parts of the base plate to which the first arm part, the second arm part, and the third arm part are fixed are unevenly located around the rotational central point in a predetermined range. For this reason, the user can easily access the movable plate from the space between the plurality of arm parts. Therefore, particularly, when the parallel link device 210 is applied to an input or output device or the like of a haptic presentation device, limitation of a range of motion of the movable plate due to interference of the user's hand or arm with the arm parts can be suppressed.

It should be understood by those skilled in the art that various modifications, combinations, sub-combinations and alterations may occur depending on design requirements and other factors insofar as they are within the scope of the appended claims or the equivalents thereof.

For example, although the three arm parts are connected between the base part and the movable member in parallel in the above-described embodiments, four or more arm parts may be provided. Here, in order to avoid interference of arm parts and facilitate control of a three-dimensional position and a three-dimensional posture using motors, a parallel link device may be constituted using three arm parts.

Also, although the axis of rotation $O_7$ of the seventh rotating joint $J_7$ is directed toward the rotational central point Q in the above-described embodiments, a technique of this disclosure is not limited to such examples. The axis of rotation $O_7$ of the seventh rotating joint $J_7$ which intersects the axis ($Ax_0$) when viewed along the axis $Ax_0$ connecting a rotational central point P to the rotational central point Q in a state in which the axis of rotation of the rotating joints of the four-joint link mechanism FL is parallel to the axis of rotation $O_7$ of the seventh rotating joint $J_7$ may not necessarily pass through the rotational central point Q.

Although the axis of rotation of the fifth rotating joint $J_5$ and the axis of rotation of the sixth rotating joint $J_6$ are orthogonal to each other in the above-described embodiments, a technique of this disclosure is not limited to such examples. The axis of rotation of the fifth rotating joint $J_5$ and the axis of rotation of the sixth rotating joint $J_6$ are not necessarily orthogonal to each other, but are preferably orthogonal to each other in terms of a structure design or control calculation. Similarly, the axis of rotation of the sixth rotating joint $J_6$ and the axis of rotation of the seventh rotating joint $J_7$ are not necessarily orthogonal to each other, but are preferably orthogonal to each other in terms of a structure design or control calculation.

Although the fixed parts of the base part to which the arm parts are coupled are disposed around the rotational central point at equal intervals every 60 degrees or every 120 degrees in the above-described embodiments, a technique of this disclosure is not limited to such examples. The fixed parts are not necessarily disposed at equal intervals, but are preferably disposed at equal intervals every 60 degrees or every 120 degrees in terms of a structure design or control calculation.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A parallel link device including:

a base part;

a plurality of arm parts each including a four-joint link mechanism coupled to the base part and a serial link mechanism, the serial link mechanism having one end side coupled to the four-joint link mechanism and including a rotating joint with four degrees of freedom; and a movable member which is coupled to the other end side of the serial link mechanism of each of the plurality of arm parts, and a position and a posture of which change along with changes of postures of the plurality of arm parts, wherein an axis of rotation ($O_7$) of a rotating joint coupled to the movable member of the serial link mechanism intersects an axis ($Ax_0$) connecting a rotational central point (P) of coupling positions between the base part and the plurality of arm parts to a rotational central point (Q) of coupling positions between the movable member and the plurality of arm parts when viewed along the axis ($Ax_0$) in a state in which an axis of rotation of a rotating joint of the four-joint link mechanism is parallel to the axis of rotation ($O_7$) of the rotating joint of the rotating joint coupled to the movable member.

(2)

The parallel link device according to (1), wherein the four-joint link mechanism includes a first link configured to rotate using a first actuator, a second link configured to rotate using a second actuator, a third link coupled to the second link through a first rotating joint, and a fourth link coupled to the third link through a second rotating joint and coupled to the first link through a third rotating joint, and an axis of rotation of the first link, an axis of rotation of the second link, an axis of rotation of the first rotating joint, an axis of rotation of the second rotating joint, and an axis of rotation of the third rotating joint are disposed to be parallel to each other.

(3)
The parallel link device according to (2), wherein
the serial link mechanism includes a fifth link coupled to the fourth link through a fourth rotating joint and a rotating joint with three degrees of freedom which is connected to a distal end side of the fifth link (4)
The parallel link device according to (3), wherein
the axis of rotation of the third rotating joint, an axis of rotation of the fourth rotating joint, and an axis of rotation of one rotating joint in the rotating joint with three degrees of freedom which is connected to the distal end side of the fifth link are orthogonal to each other, the one rotating joint being at a fifth link side.

(5)
The parallel link device according to (3) or (4), wherein axes of rotation of two rotating joints in the rotating joint with three degrees of freedom which is connected to the distal end side of the fifth link of the serial link mechanism are orthogonal to each other, the two rotating joints being at a fifth link side.

(6)
The parallel link device according to any one of (3) to (5), wherein
axes of rotation of two rotating joints in the rotating joint with three degrees of freedom which is connected to the distal end side of the fifth link of the serial link mechanism are orthogonal to each other, the two rotating joints being at a movable member side.

(7)
The parallel link device according to any one of (3) to (6), wherein
an axis of rotation of one rotating joint in the rotating joint with three degrees of freedom which is connected to the distal end side of the fifth link of the serial link mechanism of each of the plurality of arm parts intersects at one point, the one rotating joint being at a movable member side.

(8)
The parallel link device according to any one of (1) to (7), including:
three arm parts as the plurality of arm parts, wherein
coupling parts between the serial link mechanisms of the respective three arm parts and the movable member are disposed around the rotational central point of the movable member every 120 degrees.

(9)
The parallel link device according to any one of (1) to (8), including:
three arm parts as the plurality of arm parts, wherein
coupling parts between the four-joint link mechanisms of the respective three arm parts and the base part are disposed around the rotational central point of the base part every 120 degrees.

(10)
The parallel link device according to any one of (1) to (9), wherein
coupling parts between the four-joint link mechanisms of the respective plurality of arm parts and the base part are unevenly located around the rotational central point of the base part in a predetermined range.

(11)
The parallel link device according to (10), including:
three arm parts as the plurality of arm parts, wherein
coupling parts between the four-joint link mechanisms of the respective three arm parts and the base part are disposed around the rotational central point of the base part every 60 degrees.

(12)
The parallel link device according to any one of (1) to (11), including:
two actuators configured to control rotation of the four-joint link mechanism for each of the plurality of arm parts in a manner that the four-joint link mechanism has two degrees of freedom.

(13)
The parallel link device according to (12), wherein
the actuators are supported by the base part.

(14)
The parallel link device according to (12) or (13), wherein
axes of rotation of two links of the four-joint link mechanism of each of the plurality of arm parts are coaxial with each other, the two links rotating using the two actuators.

(15)
The parallel link device according to any one of (12) to (14), including:
a speed reduction mechanism configured to decelerate and transfer rotation of the actuators to the four-joint link mechanism, wherein
the speed reduction mechanism includes a wire as a rotation transferring member.

(16)
The parallel link device according to any one of (1) to (15), wherein
the four-joint link mechanism is a parallel link mechanism.

(17)
The parallel link device according to any one of (12) to (16), wherein
force feedbacks are performed through the actuators in directions of translational motions with three degrees of freedom and in directions of rotational motions with three degrees of freedom.

(18)
An industrial robot including:
a parallel link device including
a base part,
a plurality of arm parts each including a four-joint link mechanism coupled to the base part and a serial link mechanism, the serial link mechanism having one end side coupled to the four-joint link mechanism and including a rotating joint with four degrees of freedom, and
a movable member which is coupled to the other end side of the serial link mechanism of each of the plurality of arm parts, and a position and a posture of which change along with changes of postures of the plurality of arm parts, wherein
an axis of rotation ($O_7$) of a rotating joint coupled to the movable member of the serial link mechanism intersects an axis ($Ax_0$) connecting a rotational central point (P) of coupling positions between the base part and the plurality of arm parts to a rotational central point (Q) of coupling positions between the movable member and the plurality of arm parts when viewed along the axis ($Ax_0$) in a state in which an axis of rotation of a rotating joint of the four-joint link mechanism is parallel to the axis of rotation ($O_7$) of the rotating joint of the rotating joint coupled to the movable member.

(19)
A haptic presentation device including:
a parallel link device including
a base part,
a plurality of arm parts each including a four-joint link mechanism coupled to the base part and a serial link mechanism, the serial link mechanism having one end side coupled to the four-joint link mechanism and including a rotating joint with four degrees of freedom, and
a movable member which is coupled to the other end side of the serial link mechanism of each of the plurality of arm parts, and a position and a posture of which change along with changes of postures of the plurality of arm parts, wherein
an axis of rotation ($O_7$) of a rotating joint coupled to the movable member of the serial link mechanism intersects an axis ($Ax_0$) connecting a rotational central point (P) of coupling positions between the base part and the plurality of arm parts to a rotational central point (Q) of coupling positions between the movable member and the plurality of arm parts when viewed along the axis ($Ax_0$) in a state in which an axis of rotation of a rotating joint of the four-joint link mechanism is parallel to the axis of rotation ($O_7$) of the rotating joint of the rotating joint coupled to the movable member.

(20)
The haptic presentation device according to (19), wherein the haptic presentation device is a medical device capable of bilateral control.

(21) A parallel link device comprising:
a base;
a plurality of arms each having at least four degrees of freedom and each including a first arm link, a second arm link, and a rotating joint; and
a support which is coupled to an end of the second arm link of each of the plurality of arms, and a position and a posture of which changes along with changes of posture of the plurality of the arms, wherein
an axis of rotation (O7) of the rotating joint, which is coupled to the support and the second arm link, intersects or is adjacent to a rotational central point (Q) of the support.

(22)
The parallel link device according to (21), wherein the first arm link includes
a first link configured to rotate using a first actuator,
a second link configured to rotate using a second actuator,
a third link coupled to the second link through a first rotating joint, and
a fourth link coupled to the third link through a second rotating joint and coupled to the first link through a third rotating joint, and
a first axis of rotation of the first link, a second axis of rotation of the second link, a third axis of rotation of the first rotating joint, a fourth axis of rotation of the second rotating joint, and a fifth axis of rotation of the third rotating joint are disposed to be parallel to each other.

(23)
The parallel link device according to (22), wherein the second arm link includes a fifth link coupled to the fourth link through a fourth rotating joint and coupled to a support rotating joint with three degrees of freedom which is connected to a distal end side of the fifth link.

(24)
The parallel link device according to (21)-(23), wherein the fifth axis of rotation of the third rotating joint and a sixth axis of rotation of the fourth rotating joint, and a seventh axis of rotation of a fifth rotating joint included in the support rotating joint with three degrees of freedom which is connected to the distal end side of the fifth sub link, are orthogonal to each other, the fifth rotating joint being at a fifth link side.

(25)
The parallel link device according to (21)-(24), wherein axes of rotation of the fifth rotating joint and a sixth rotating joint included in the support rotating joint with three degrees of freedom which is connected to the distal end side of the fifth link of the second arm link, are orthogonal to each other.

(26)
The parallel link device according to (21)-(25), wherein axes of rotation of the rotating joint and the seventh rotating joint included in the rotating joint with three degrees of freedom which is connected to the distal end side of the fifth link of the second arm link are orthogonal to each other.

(27)
The parallel link device according to (21)-(23), wherein the axis of rotation of the rotating joint included in the support rotating joint with three degrees of freedom which is connected to the distal end side of the fifth link of the second arm link mechanism for each of the plurality of the arms intersects at the rotational central point (Q).

(28)
The parallel link device according to (21)-(27), wherein the plurality of the arms includes three arms, and
wherein first couplings between the second arm links of the respective three arms and the support are disposed around the rotational central point (Q) of the support every 120 degrees.

(29)
The parallel link device according to (21)-(28), wherein second couplings between the respective three arms and the base are disposed around a rotational central point of the base every 120 degrees.

(30)
The parallel link device according to (21)-(28), wherein second couplings between the first arm links of the respective three arms and the base are unevenly located around a rotational central point of the base within a predetermined range.

(31)
The parallel link device according to (21)-(28), wherein second couplings between the first arm links of the respective three arms and the base are disposed around the rotational central point of the base every 60 degrees.

(32)
The parallel link device according to (21)-(31), comprising:
two actuators configured to control rotation of the first arm link for each of the plurality of arms in a manner that the first arm link has two degrees of freedom.

(33)
The parallel link device according to (32), wherein the actuators are supported by the base.

(34)
The parallel link device according to (32)-(33), wherein axes of rotation of two links of the first arm link of each of the plurality of arms are coaxial with each other, the two links rotating using the two actuators.

(35)
The parallel link device according to (32)-(34), comprising:
a brake configured to decelerate and transfer rotation of the actuators to the first arm link, wherein
the brake uses a wire to transfer rotation.

(36)
The parallel link device according to (21)-(35), wherein the first arm link is a parallel link.
(37)
The parallel link device according to (32)-(36), wherein force feedbacks are performed through the actuators in directions of translational motion with three degrees of freedom and in directions of rotational motion with three degrees of freedom.
(38)
The parallel link device according to (21), wherein
the axis of rotation (O7) of the rotating joint, which is coupled to the support and the second arm link intersects an axis (Ax0) connecting a rotational central point (P) of the base to the rotational central point (Q) of the support when viewed along the axis (Ax0) in a state in which an axis of rotation of a rotating joint of the first arm link mechanism is parallel to the axis of rotation (O7) of the rotating joint.
(39)
An industrial robot comprising:
a parallel link device including
a base;
a plurality of arms each having at least four degrees of freedom and each including a first arm link, a second arm link, and a rotating joint; and
a support which is coupled to an end of the second arm link of each of the plurality of the arms, and a position and a posture of which changes along with changes of posture of the plurality of the arms, wherein
an axis of rotation (O7) of the rotating joint, which is coupled to the support and the second arm link, intersects or is adjacent to a rotational central point (Q) of the support.
(40)
A haptic presentation device comprising:
a parallel link device including
a base;
a plurality of arms each having at least four degrees of freedom and each including a first arm link, a second arm link, and a rotating joint; and
a support which is coupled to an end of the second arm link of each of the plurality of the arms, and a position and a posture of which changes along with changes of posture of the plurality of the arms, wherein
an axis of rotation (O7) of the rotating joint that is coupled to the support and the second arm link intersects or is adjacent to a rotational central point (Q) of the support.
(41)
The haptic presentation device according to (40), wherein the haptic presentation device is a medical device capable of bilateral control.

REFERENCE SIGNS LIST 10 parallel link device
30 base part
40 movable member
50a first arm part
50b second arm part
50c third arm part
110 parallel link device
130 base part (base plate)
140 movable member (movable plate)
150a first arm part
150b second arm part
150c third arm part
FL four-joint link mechanism
SL serial link mechanism
$J_7$ seventh rotating joint
$O_7$ axis of rotation
$Ax_0$ axis
P, Q rotational central point

The invention claimed is:
1. A parallel link device comprising:
a base;
a plurality of arms each having at least four degrees of freedom and each including a first arm link, a second arm link, and a rotating joint; and
a support which is coupled to an end of the second arm link of each of the plurality of the arms, and a position and a posture of which changes along with changes of posture of the plurality of the arms, wherein
an axis of rotation (O7) of the rotating joint, which is coupled to the support and the second arm link, intersects or is adjacent to a rotational central point of the support,
the plurality of the arms includes three arms,
first couplings between the second arm links of the respective three arms and the support are disposed around the rotational central point (Q) of the support every 120 degrees, and
second couplings between the first arm links of the respective three arms and the base are unevenly located around a rotational central point of the base within a predetermined range, or
second couplings between the first arm links of the respective three arms and the base are disposed around the rotational central point of the base every 60 degrees.
2. The parallel link device according to claim 1, wherein the first arm link includes
a first link configured to rotate using a first actuator,
a second link configured to rotate using a second actuator,
a third link coupled to the second link through a first rotating joint, and
a fourth link coupled to the third link through a second rotating joint and coupled to the first link through a third rotating joint, and
a first axis of rotation of the first link, a second axis of rotation of the second link, a third axis of rotation of the first rotating joint, a fourth axis of rotation of the second rotating joint, and a fifth axis rotation of the third rotating joint are disposed to be parallel to each other.
3. The parallel link device according to claim 2, wherein the second arm link includes a fifth link coupled to the fourth link through a fourth rotating joint and coupled to a support rotating joint, which, with the rotating joint, provides three degrees of freedom, the support rotating joint being connected to a distal end side of the fifth link.
4. The parallel link device according to claim 3, wherein the fifth axis of rotation of the third rotating joint and a sixth axis of rotation of the fourth rotating joint, and a seventh axis of rotation of a fifth rotating joint included in the support rotating joint with three degrees of freedom which is connected to the distal end side of the fifth link, are orthogonal to each other, the fifth rotating joint being at a fifth link side.
5. The parallel link device according to claim 4, wherein axes of rotation of the fifth rotating joint and a sixth rotating joint included in the support rotating joint with three degrees of freedom which is connected to the distal end side of the fifth link of the second arm link, are orthogonal to each other.

6. The parallel link device according to claim 5, wherein axes of rotation of the rotating joint and the sixth rotating joint included in the rotating joint with three degrees of freedom which is connected to the distal end side of the fifth link of the second arm link are orthogonal to each other.

7. The parallel link device according to claim 3, wherein the axis of rotation of the rotating joint included in the support rotating joint with three degrees of freedom which is connected to the distal end side of the fifth link of the second arm link for each of the plurality of the arms intersects at the rotational central point (Q).

8. The parallel link device according to claim 1, comprising:
two actuators configured to control rotation of the first arm link for each of the plurality of arms in a manner that the first arm link has two degrees of freedom.

9. The parallel link device according to claim 8, wherein the actuators are supported by the base.

10. The parallel link device according to claim 8, wherein axes of rotation of two links of the first arm link of each of the plurality of arms are coaxial with each other, the two links rotating using the two actuators.

11. The parallel link device according to claim 8, comprising:
a brake configured to decelerate and transfer rotation of the actuators to the first arm link, wherein the brake uses a wire to transfer rotation.

12. The parallel link device according to claim 1, wherein the first arm link is a parallel link.

13. The parallel link device according to claim 8, wherein force feedbacks are performed through the actuators in directions of translational motion with three degrees of freedom and in directions of rotational motion with three degrees of freedom.

14. The parallel link device according to claim 1, wherein the axis of rotation (O7) of the rotating joint, which is coupled to the support and the second arm link intersects an axis (Ax0) connecting a rotational central point (P) of the base to the rotational central point (Q) of the support when viewed along the axis (Ax0) in a state in which an axis of rotation of a rotating joint of the first arm link mechanism is parallel to the axis of rotation (O7) of the rotating joint.

15. An industrial robot comprising:
a parallel link device including
a base;
a plurality of arms each having at least four degrees of freedom and each including a first arm link, a second arm link, and a rotating joint; and
a support which is coupled to an end of the second arm link of each of the plurality of the arms, and a position and a posture of which changes along with changes of posture of the plurality of the arms, wherein
an axis of rotation (O7) of the rotating joint, which is coupled to the support and the second arm link, intersects or is adjacent to a rotational central point (Q) of the support, and
the plurality of the arms includes three arms,
first couplings between the second arm links of the respective three arms and the support are disposed around the rotational central point (Q) of the support every 120 degrees, and
second couplings between the first arm links of the respective three arms and the base are unevenly located around a rotational central point of the base within a predetermined range, or
second couplings between the first arm links of the respective three arms and the base are disposed around the rotational central point of the base every 60 degrees.

16. A haptic presentation device comprising:
a parallel link device including
a base;
a plurality of arms each having at least four degrees of freedom and each including a first arm link, a second arm link, and a rotating joint; and
a support which is coupled to an end of the second arm link of each of the plurality of the arms, and a position and a posture of which changes along with changes of posture of the plurality of the arms, wherein
an axis of rotation (O7) of the rotating joint that is coupled to the support and the second arm link intersects or is adjacent to a rotational central point (Q) of the support, and
the plurality of the arms includes three arms,
first couplings between the second arm links of the respective three arms and the support are disposed around the rotational central point (Q) of the support every 120 degrees, and
second couplings between the first arm links of the respective three arms and the base are unevenly located around a rotational central point of the base within a predetermined range, or
second couplings between the first arm links of the respective three arms and the base are disposed around the rotational central point of the base every 60 degrees.

17. The haptic presentation device according to claim 16, wherein
the haptic presentation device is a medical device capable of bilateral control.

* * * * *